United States Patent
Gibbs et al.

(10) Patent No.: US 9,249,091 B2
(45) Date of Patent: Feb. 2, 2016

(54) POST-TREATED SULFURIZED SALT OF AN ALKYL-SUBSTITUTED HYDROXYAROMATIC COMPOSITION

(71) Applicants: Andrew R. Gibbs, Pleasant Hill, CA (US); Curtis Campbell, Hercules, CA (US)

(72) Inventors: Andrew R. Gibbs, Pleasant Hill, CA (US); Curtis Campbell, Hercules, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 194 days.

(21) Appl. No.: 13/727,892

(22) Filed: Dec. 27, 2012

(65) Prior Publication Data

US 2013/0165359 A1    Jun. 27, 2013

Related U.S. Application Data

(60) Provisional application No. 61/580,562, filed on Dec. 27, 2011.

(51) Int. Cl.
| | | |
|---|---|---|
| C07C 307/00 | (2006.01) | |
| C10M 159/16 | (2006.01) | |
| C07G 99/00 | (2009.01) | |

(52) U.S. Cl.
CPC .............. *C07C 307/00* (2013.01); *C07G 17/00* (2013.01); *C10M 159/16* (2013.01);
(Continued)

(58) Field of Classification Search
CPC .................................................. C07C 307/00
USPC .......................................... 508/561; 564/305
See application file for complete search history.

(56) References Cited

U.S. PATENT DOCUMENTS

| | | |
|---|---|---|
| 2,459,116 A | 1/1949 | Oberright |
| 3,036,003 A | 5/1962 | Verdol |

(Continued)

FOREIGN PATENT DOCUMENTS

| | | |
|---|---|---|
| CA | 1094053 A | 1/1981 |
| CA | 1099744 A | 4/1981 |

(Continued)

OTHER PUBLICATIONS

Tomiyasu et al. (JPH06264080; machine translation); Bib Translated.*

(Continued)

*Primary Examiner* — Prem C Singh
*Assistant Examiner* — Chantel Graham
(74) *Attorney, Agent, or Firm* — M. Carmen & Associates, PLLC

(57) ABSTRACT

Disclosed herein is a post-treated salt of a sulfurized alkyl-substituted hydroxyaromatic composition which is a reaction product of (a) a salt of a sulfurized alkyl-substituted hydroxyaromatic composition, wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof, (b) a source of an aldehyde and (c) a primary and/or secondary monoamine compound having at least one active hydrogen. The post-treated salt of a sulfurized alkylhydroxyaromatic composition disclosed herein has a reduced content of unsulfurized alkyl-substituted hydroxyaromatic compound and its unsulfurized metal salt as compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

25 Claims, 1 Drawing Sheet

(52) U.S. Cl.
CPC ..... *C10M 2217/043* (2013.01); *C10N 2230/64* (2013.01); *C10N 2240/04* (2013.01); *C10N 2240/08* (2013.01); *C10N 2240/10* (2013.01); *C10N 2240/102* (2013.01); *C10N 2240/30* (2013.01); *C10N 2250/10* (2013.01); *C10N 2260/10* (2013.01)

(56) References Cited

U.S. PATENT DOCUMENTS

| | | |
|---|---|---|
| 3,172,892 A | 3/1965 | Suer et al. |
| 3,219,666 A | 11/1965 | Norman et al. |
| 3,272,746 A | 9/1966 | Suer et al. |
| 3,275,554 A | 9/1966 | Wagenaar |
| 3,329,658 A | 7/1967 | Fields |
| 3,438,757 A | 4/1969 | Honnen et al. |
| 3,449,250 A | 6/1969 | Fields |
| 3,454,555 A | 7/1969 | Van Der Voort et al. |
| 3,565,804 A | 2/1971 | Honnen et al. |
| 3,586,629 A | 6/1971 | Otto et al. |
| 3,591,598 A | 7/1971 | Traise et al. |
| 3,649,229 A | 3/1972 | Otto |
| 3,666,730 A | 5/1972 | Coleman |
| 3,980,569 A | 9/1976 | Pindar et al. |
| 4,088,586 A | 5/1978 | Wilgus et al. |
| 4,157,308 A | 6/1979 | King et al. |
| 4,157,309 A | 6/1979 | King et al. |
| 4,161,475 A | 7/1979 | Davis |
| 4,175,044 A | 11/1979 | King et al. |
| 4,219,430 A | 8/1980 | Vaughan |
| 4,234,435 A | 11/1980 | Meinhardt et al. |
| 4,305,832 A | 12/1981 | Braid |
| 4,612,132 A | 9/1986 | Wollenberg et al. |
| 4,746,446 A | 5/1988 | Wollenberg et al. |
| 4,861,504 A | 8/1989 | Chao |
| 4,889,646 A | 12/1989 | Vettel |
| 5,320,765 A | 6/1994 | Fetterman, Jr. et al. |
| 5,326,488 A | 7/1994 | Minokami et al. |
| 5,716,912 A | 2/1998 | Harrison et al. |
| 6,165,235 A | 12/2000 | Kolp et al. |
| 6,372,696 B1 | 4/2002 | Tipton |
| 6,440,905 B1 | 8/2002 | Epps et al. |
| 2008/0070818 A1 | 3/2008 | Arrowsmith et al. |
| 2009/0143264 A1 | 6/2009 | Harrison et al. |
| 2011/0118160 A1 | 5/2011 | Campbell et al. |
| 2011/0124539 A1* | 5/2011 | Sinquin .............. C10M 159/22 508/567 |
| 2011/0245121 A1 | 10/2011 | Tobias et al. |

FOREIGN PATENT DOCUMENTS

| | | |
|---|---|---|
| CN | 101215248 | 7/2008 |
| EP | 1712570 A1 | 10/2006 |
| GB | 1345030 | 1/1974 |
| GB | 1518283 | 7/1978 |
| GB | 1604609 A | 12/1981 |
| JP | H06264080 * | 9/1994 |

OTHER PUBLICATIONS

Tomiyasu et al. (JPH06264080; machine translation); Claims Translated.*

Tomiyasu et al. (JPH06264080; machine translation); Description Translated.*

The International Search Report issued in counterpart International Patent Application No. PCT/US2012/071753.

Singapore Search Report issued in counterpart Singapore Application No. 11201403578W dated Nov. 6, 2014.

Mortier, et al. Chemistry and Technology of Lubricants, 2nd Edition, London, Springer (1996), Chapter 3, pp. 75-85, Chapter 6, pp. 187-196.

Chinese Office Action issued in counterpart Chinese Patent Application No. 20128 2330.2 dated Aug. 12, 2015.

European Search Report issued in counterpart European Patent Application No. 12873493.6 dated Jul. 15, 2015.

* cited by examiner

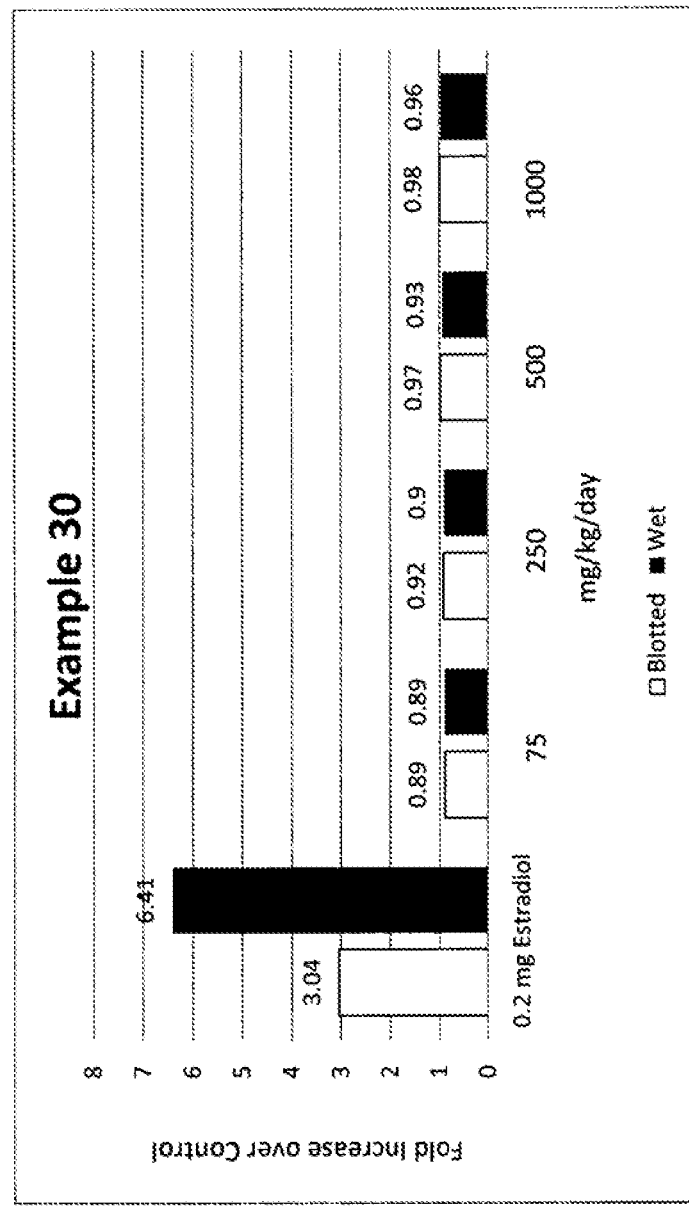

POST-TREATED SULFURIZED SALT OF AN ALKYL-SUBSTITUTED HYDROXYAROMATIC COMPOSITION

PRIORITY

This application claims the benefit under 35 U.S.C. 119 to U.S. Provisional Patent Application No. 61/580,562, filed on Dec. 27, 2011, the contents of which are incorporated by reference herein.

BACKGROUND OF THE INVENTION

1. Technical Field

The present invention generally relates to a post-treated sulfurized salt of an alkyl-substituted hydroxyaromatic composition. The present invention further relates to a post-treated sulfurized salt of an alkyl-substituted hydroxyaromatic composition having a reduced content of unsulfurized alkyl-substituted hydroxyaromatic compound and its unsulfurized metal salt, methods of making same and their use in lubricating oil compositions.

2. Description of the Related Art

The lubricant additive industry generally uses alkyl phenols (e.g., tetrapropenyl phenol, TPP) to prepare detergents comprising sulfurized metal alkyl phenate. Metal salts of sulfurized alkylphenols are useful lubricating oil additives which impart detergency and dispersancy properties to the lubricating oil composition for marine, automotive, railroad and air-cooled engines as well as providing for an alkalinity reserve in the oil. Alkalinity reserve is necessary in order to neutralize acids generated during engine operation. Without this alkalinity reserve, the acids so generated would result in harmful engine corrosion. However, there may be some unreacted alkyl phenols such as tetrapropenyl phenol present in the sulfurized metal alkyl phenate as well as in lubricating oils containing one or more of the sulfurized metal alkyl phenates.

A recent reproductive toxicity study in rats sponsored by the Petroleum Additives Panel of the American Chemistry Council shows that free or unreacted TPP may cause adverse effects on male and female reproductive organs. Further, it is believed that TPP may be corrosive or irritating to the skin.

U.S. Patent Application Publication No. 20080070818 ("the '818 publication") discloses a lubricating oil composition including at least one sulphurized overbased metal phenate detergent prepared from a $C_9$-$C_{15}$ alkyl phenol, at least one sulphurizing agent, at least one metal and at least one overbasing agent; the detergent including less than 6.0% by combined mass of unsulphurized $C_9$-$C_{15}$ alkyl phenol and unsulphurized metal salts thereof. Examples A and B disclosed in the '818 publication obtained an overbased detergent having 5.58 and 3.84 mass %, respectively, of unsulphurized alkyl phenol and its unsulphurized calcium salt.

U.S. Patent Application Publication No. 20090143264 ("the '264 publication") discloses sulfurized metal alkyl phenate compositions having a low alkyl phenol content. The sulfurized metal alkyl phenate compositions of the '264 publication can be prepared by reacting a phenol compound such as tetrapropenyl phenol with an aldehyde to form a phenolic resin and then reacting the phenolic resin simultaneously with a metal base and a first sulfurizing agent.

U.S. Pat. No. 3,649,229 ("the '229 patent") discloses a condensation product of (1) a high molecular weight alkyl-substituted hydroxyaromatic compound, wherein the alkyl group has a molecular weight from about 600 to about 3,000; (2) an amine which contains a HN< group, i.e., an active hydrogen, and (3) an aldehyde, wherein the respective molar ratio of the reactants is 1:0.1-10:0.1-10. Example 7 of the '229 patent discloses that Mannich reaction of polypropylphenol sulfide with diethylenetriamine and paraformaldehyde.

U.S. Pat. No. 4,088,586 ("the '586 patent") discloses a Mannich base prepared by condensing tetrapropenylphenol, formaldehyde and diethylenetriamine. The '586 patent further discloses that the calcium salt of the Mannich base is prepared using conventional methods, for example, by treating the Mannich base with calcium hydroxide in the presence of a promoter.

U.S. Pat. No. 4,157,308 discloses Mannich bases and the alkaline earth metal salts thereof which are prepared by condensing formaldehyde and a polyamine with a phenolic mixture consisting of (1) from 95 to 30% phenol alkylated with a propylene tetramer and (2) from 5 to 70% phenol alkylated with a straight-chain alpha-olefin of from 16 to about 28 carbon atoms or alpha-olefin mixtures wherein the alpha-olefins are of from 16 to about 28 carbon atoms.

U.S. Pat. No. 4,157,309 discloses Mannich bases and the alkaline earth metal salts thereof, which are prepared by condensing formaldehyde and a polyamine with a sulfur-containing phenolic mixture consisting of (1) from 5 to 35 mol percent of a sulfurized alkylphenol wherein the alkyl group is $C_8$-$C_{36}$ alkyl, and (2) from 95 to 65 mol percent of phenol alkylated with a propylene tetramer.

U.S. Pat. No. 4,175,044 discloses Mannich bases and the alkaline earth metal salts thereof, which are prepared by condensing formaldehyde and a polyamine with a sulfur-containing phenolic mixture consisting of (1) from 5 to 40% of a sulfurized alkylphenol wherein the alkyl group is $C_8$-$C_{36}$ alkyl, and (2) from 95 to 60% of a phenolic mixture consisting of (a) from 95 to 30% phenol alkylated with a propylene tetramer and (b) from 5 to 70% phenol alkylated with a straight-chain alpha-olefin of from 16 to about 28 carbon atoms or alpha-olefin mixtures wherein the alpha-olefins are of from 16 to about 28 carbon atoms.

GB1604609 discloses in Examples G and 2 the condensation product of a mixture of alkyl phenol and a carbonated and non carbonated sulfurized alkylphenol/salt mixture, diethylamide triamine, and paraformaldehyde.

However, problems associated with the use of a polyamine in preparing a Mannich reaction product includes formation of sediment and plugging issues due to the multiple reactions occurring from the highly reactive polyamine, as well as being too viscous a material.

To reduce any potential health risks to customers and to avoid potential regulatory issues, there is a need to reduce the amount of free unsulfurized alkyl-substituted hydroxyaromatic compound and its metal salt in the salts of sulfurized alkyl-substituted hydroxyaromatic compositions. Accordingly, it is desirable to provide an improved process for making post-treated salts of sulfurized alkyl-substituted hydroxyaromatic compositions which have relatively low levels of unsulfurized alkyl-substituted hydroxyaromatic compound and its metal salt.

SUMMARY OF THE INVENTION

In accordance with one embodiment of the present invention, there is provided a post-treated salt of a sulfurized alkyl-substituted hydroxyaromatic composition which is a reaction product of (a) a salt of a sulfurized alkyl-substituted hydroxyaromatic composition, wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof (b) a source of an aldehyde and (c) a primary and/or secondary monoamine compound having at least one active hydrogen.

In accordance with a second embodiment of the present invention, there is provided a post-treated salt of a sulfurized alkyl-substituted hydroxyaromatic composition having a reduced content, by combined mass, of an unsulfurized alkyl-substituted hydroxyaromatic compound and its unsulfurized metal salt, the post-treated salt of the sulfurized alkyl-substituted hydroxyaromatic composition being prepared by a process comprising:

(a) providing a salt of a sulfurized alkyl-substituted hydroxyaromatic composition containing an unsulfurized alkyl-substituted hydroxyaromatic compound and its unsulfurized metal salt; wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof; and (b) reacting the salt of a sulfurized alkyl-substituted hydroxyaromatic composition with an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

In accordance with a third embodiment of the present invention, there is provided a process for preparing a post-treated salt of a sulfurized alkyl-substituted hydroxyaromatic composition having a reduced content of unsulfurized alkyl-substituted hydroxyaromatic compound and its unsulfurized metal salt, the process comprising the steps of:

(a) providing a salt of a sulfurized alkyl-substituted hydroxyaromatic composition containing an unsulfurized alkyl-substituted hydroxyaromatic compound and its unsulfurized metal salt; wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof; and (b) reacting the salt of a sulfurized alkyl-substituted hydroxyaromatic composition with an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

In accordance with a fourth embodiment of the present invention, there is provided a lubricating oil composition comprising:

(a) a major amount of an oil of lubricating viscosity; and (b) at least one post-treated salt of a sulfurized alkyl-substituted hydroxyaromatic composition which is a reaction product of (i) a salt of a sulfurized alkyl-substituted hydroxyaromatic composition, wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof, (ii) a source of an aldehyde and (iii) a primary and/or secondary monoamine compound having at least one active hydrogen.

In accordance with a fifth embodiment of the present invention, there is provided a lubricating oil composition comprising:

(a) a major amount of an oil of lubricating viscosity; and (b) at least one post-treated salt of a sulfurized alkyl-substituted hydroxyaromatic composition having a reduced content, by combined mass, of an unsulfurized alkyl-substituted hydroxyaromatic compound and its unsulfurized metal salt, the salt of a sulfurized alkylhydroxyaromatic composition being produced by a process comprising:

(i) providing a salt of a sulfurized alkyl-substituted hydroxyaromatic composition containing an unsulfurized alkyl-substituted hydroxyaromatic compound and its unsulfurized metal salt; wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof; and (ii) reacting the salt of a sulfurized alkyl-substituted hydroxyaromatic composition with an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

In accordance with a sixth embodiment of the present invention, there is provided a method of operating an internal combustion engine comprising operating the internal combustion engine with a lubricating oil composition comprising:

(a) a major amount of an oil of lubricating viscosity; and (b) at least one post-treated salt of a sulfurized alkyl-substituted hydroxyaromatic composition which is a reaction product of (i) a salt of a sulfurized alkyl-substituted hydroxyaromatic composition, wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof, (ii) a source of an aldehyde and (iii) a primary and/or secondary monoamine compound having at least one active hydrogen.

In accordance with a seventh embodiment of the present invention, there is provided a method of operating an internal combustion engine comprising operating the internal combustion engine with a lubricating oil composition comprising:

(a) a major amount of an oil of lubricating viscosity; and (b) at least one post-treated salt of a sulfurized alkyl-substituted hydroxyaromatic composition having a reduced content, by combined mass, of an unsulfurized alkyl-substituted hydroxyaromatic compound and its unsulfurized metal salt, the post-treated salt of a sulfurized alkylhydroxyaromatic composition being produced by a process comprising:

(i) providing a salt of a sulfurized alkyl-substituted hydroxyaromatic composition containing an unsulfurized alkyl-substituted hydroxyaromatic compound and its unsulfurized metal salt; wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof; and (ii) reacting the salt of a sulfurized alkyl-substituted hydroxyaromatic composition with an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

In accordance with a eighth embodiment of the present invention, there is provided a method for reducing the endocrine disrupting properties of a lubricating oil composition on exposure to mammals, the method comprising adding at least one post-treated salt of a sulfurized alkyl-substituted hydroxyaromatic composition which is a reaction product of (i) a salt of a sulfurized alkyl-substituted hydroxyaromatic composition, wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof, (ii) a source of an aldehyde and (iii) a primary and/or secondary monoamine compound having at least one active hydrogen, to a lubricating oil composition comprising a major amount of an oil of lubricating viscosity.

In accordance with a ninth embodiment of the present invention, there is provided a method for reducing the endocrine disrupting properties of a lubricating oil composition on exposure to mammals, the method comprising adding at least one post-treated salt of a sulfurized alkylhydroxyaromatic composition which is produced by a process comprising:

(i) providing a salt of a sulfurized alkyl-substituted hydroxyaromatic composition containing an unsulfurized alkyl-substituted hydroxyaromatic compound and its unsulfurized metal salt; wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof; and (ii) reacting the salt of a sulfurized alkyl-substituted hydroxyaromatic composition with an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition, to a lubricating oil composition comprising a major amount of an oil of lubricating viscosity.

The process of the present invention advantageously provides a post-treated salt of a sulfurized alkyl-substituted hydroxyaromatic composition containing relatively low levels of unsulfurized alkyl-substituted hydroxyaromatic compound and its unsulfurized metal salt that can be prepared in a simple, cost efficient manner. This is an unexpected improvement in that the presence of the unsulfurized alkyl-substituted hydroxyaromatic compound and its unsulfured metal salt in a salt of a sulfurized alkyl-substituted hydroxyaromatic composition is undesirable because of their deleterious estrogenic behavior and there is a growing concern of their potential release in the environment.

BRIEF DESCRIPTION OF THE DRAWINGS

FIG. 1 is a bar graph showing the difference in mean blotted and wet uterine weights for the four treatment groups (75, 250, 500, and 1000 mg/kg/day) compared to the vehicle control group.

DETAILED DESCRIPTION OF THE PREFERRED EMBODIMENTS

Prior to discussing the invention in further detail the following terms will be defined:

Definitions

As used herein, the following terms have the following meanings, unless expressly stated to the contrary:

The term "lime" as used herein refers to calcium hydroxide, also known as slaked lime or hydrated lime.

The term "Total Base Number" or "TBN" as used herein refers to the amount of base equivalent to milligrams of KOH in 1 gram of sample. Thus, higher TBN numbers reflect more alkaline products, and therefore a greater alkalinity reserve. The TBN of a sample can be determined by ASTM Test No. D2896-11 issued May 15, 2011 or any other equivalent procedure.

The term "phenate" means a metal salt of a phenol.

The term, "alkylphenate" means a metal salt of an alkylphenol.

The term "alkylphenol" means a phenol having one or more alkyl substituents, wherein at least one of the alkyl substituents has a sufficient number of carbon atoms to impart oil solubility to the phenol.

The term "lime" refers to calcium hydroxide, also known as slaked lime or hydrated lime.

The term "metal" means alkali metals, alkaline earth metals, or mixtures Thereof.

The term "alkaline earth metal" refers to calcium, barium, magnesium, and strontium.

The term "alkali metal" refers to lithium, sodium, potassium, rubidium, and cesium.

The term "metal base" refers to a metal hydroxide, metal oxide, metal alkoxides and the like and mixtures thereof, wherein the metal is an alkaline earth metal or alkali metal.

The term "overbased" refers to a class of metal salts or complexes. These materials have also been referred to as "basic", "superbased", "hyperbased", "complexes", "metal complexes", "high-metal containing salts", and the like. Overbased products are metal salts or complexes characterized by a metal content in excess of that which would be present according to the stoichiometry of the metal and the particular acidic organic compound reacted with the metal, e.g., a carboxylic acid. Suitable overbasing metals include alkaline earth metals such as magnesium, calcium, barium, and strontium. Suitable overbasing metals can be provided from the corresponding metal hydroxides, for example, calcium hydroxide and magnesium hydroxide provide the source for the alkaline earth metals calcium and magnesium, respectively. Additional overbasing can be achieved by the addition of acidic overbasing compounds for example, carbon dioxide and boric acid.

The term "sulfated ash content" refers to the amount of metal-containing additives (e.g., calcium, magnesium, molybdenum, zinc, etc.) in a lubricating oil composition and is typically measured according to ASTM D874, which is incorporated herein by reference.

The present invention is directed to a post-treated salt of a sulfurized alkyl-substituted hydroxyaromatic composition which is a reaction product of (a) a salt of a sulfurized alkyl-substituted hydroxyaromatic composition, wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof, (b) a source of an aldehyde and (c) a primary and/or secondary monoamine compound having at least one active hydrogen.

In another embodiment, the present invention is further directed to a post-treated salt of a sulfurized alkyl-substituted hydroxyaromatic composition having a reduced content of at least about 70%, by combined mass, of an unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxy aromatic composition.

In general, the post-treated salt of a sulfurized alkyl-substituted hydroxyaromatic composition is obtained by (a) providing a salt of a sulfurized alkyl-substituted hydroxyaromatic composition containing an unsulfurized alkyl-substituted hydroxyaromatic compound and its unsulfurized metal salt; wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof; and (b) reacting the salt of a sulfurized alkyl-substituted hydroxyaromatic composition an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

In step (a), a salt of a sulfurized alkyl-substituted hydroxyaromatic composition containing an unsulfurized alkyl-substituted hydroxyaromatic compound and its unsulfurized metal salt is provided. In general, the composition is obtained by (i) alkylating a hydroxyaromatic compound with one or more olefins comprising $C_9$ to $C_{18}$ oligomers of monomers selected from propylene, butylene or mixtures thereof, to provide an alkyl-substituted hydroxyaromatic compound; (ii) sulfurizing and neutralizing the alkyl-substituted hydroxyaromatic compound in any order to provide a salt of a sulfurized alkyl-substituted hydroxyaromatic composition; and (iii) optionally overbasing the salt of a sulfurized alkyl-substituted hydroxyaromatic composition. In one embodiment, the unsulfurized alkyl-substituted hydroxyaromatic compound is tetrapropenyl phenol. In certain embodiments, the tetrapropenyl phenol comprises a mixture of the isomers of tetrapropenyl phenol, such as a mixture of p-dodecylphenol, m-dodecylphenol and o-dodecylphenol.

The alkyl-substituted hydroxyaromatic compound employed in the present invention is prepared by methods that are well known in the art. Useful hydroxyaromatic compounds that may be alkylated include mononuclear monohydroxy and polyhydroxy aromatic hydrocarbons having 1 to 4, and preferably 1 to 3, hydroxyl groups. Suitable hydroxyaromatic compounds include phenol, catechol, resorcinol, hydroquinone, pyrogallol, cresol, and the like and mixtures thereof. In one embodiment, the hydroxyaromatic compound is a phenol.

The alkylating agent employed to alkylate the hydroxyaromatic compound includes one or more olefins comprising $C_9$ to $C_{18}$ oligomers of monomers selected from propylene, butylene or mixtures thereof. Generally, the one or more olefins will contain a major mount of the $C_9$ to $C_{18}$ oligomers of monomers selected from propylene, butylene or mixtures thereof. Examples of such olefins include propylene tetramer, butylene trimer and the like. As one skilled in the art will readily appreciate, other olefins may be present. For example, the other olefins that can be used in addition to the $C_9$ to $C_{18}$ oligomers include linear olefins, cyclic olefins, branched olefins other than propylene oligomers such as butylene or isobutylene oligomers, arylalkylenes and the like and mixtures thereof. Suitable linear olefins include 1-hexene, 1-nonene, 1-decene, 1-dodecene and the like and mixtures thereof. Especially suitable linear olefins are high, molecular weight normal alpha-olefins such as $C_{16}$ to $C_{30}$ normal alpha-olefins, which can be obtained from, processes such as ethylene oligomerization or wax cracking. Suitable cyclic olefins include cyclohexene, cyclopentene, cyclooctene and the like and mixtures thereof. Suitable branched olefins include butylene dimer or trimer or higher molecular weight isobutylene oligomers, and the like and mixtures thereof. Suitable arylalkylenes include styrene, methyl styrene, 3-phenylpropene, 2-phenyl-2-butene and the like and mixtures thereof.

Alkylation of the hydroxyaromatic compound with the one or more olefins comprising $C_9$ to $C_{18}$ oligomers of monomers selected from propylene, butylene or mixtures thereof is generally carried out in the presence of an alkylation catalyst. Useful alkylation catalysts include Lewis acid catalysts, solid acid catalysts, trifluorormethanesulfonic acid, and acidic molecular sieve catalysts. Suitable Lewis acid catalysts include aluminum trichloride, aluminum tribromide, aluminum triiodide, boron trifluoride, boron tribromide, boron triiodide and the like.

Suitable solid acidic catalysts include zeolites, acid clays, and/or silica-alumina. The catalyst may be a molecular sieve. Eligible molecular sieves are silica-aluminophosphate molecular sieves or metal silica-aluminophosphate molecular sieves, in which the metal may be, for example, iron, cobalt or nickel. In one embodiment, a solid catalyst is a cation exchange resin in its acid form, for example, crosslinked sulfonic acid catalyst. Suitable sulfonated acidic ion exchange resin type catalysts include Amberlyst 36®, available from Rohm and Hass (Philadelphia, Pa.). The acid catalyst may be recycled or regenerated when used in a batch process or a continuous process.

The reaction conditions for the alleviation depend upon the type of catalyst used, and any suitable set of reaction conditions that result in high conversion to the alkyl hydroxyaromatic product can be employed. Typically, the reaction temperature for the alkylation reaction will be in the range of about 25° C. to about 200° C. and preferably from, about 85° C. to about 135° C. The reaction pressure will generally be atmospheric, although higher or lower pressures may be employed. The alkylation process can be practiced in a batch wise, continuous or semi-continuous manner. The molar ratio of the hydroxyaromatic compound to one or more olefins is normally in the range of about 10:1 to about 0.5:1, and preferably will be in the range of about 5:1 to about 3:1.

The alkylation reaction may be carried out neat or in the presence of a solvent which is inert to the reaction of the hydroxyaromatic compound and the olefin mixture. When employed, a typical solvent is hexane.

Upon completion of the reaction, the desired alkylhydroxyaromatic compound can be isolated using conventional techniques. Typically, excess hydroxyaromatic compound is distilled from the reaction product.

The alkyl group of the alkylhydroxyaromatic compound is typically attached to the hydroxyaromatic compound primarily in the ortho and para positions, relative to the hydroxyl group.

The alkyl-substituted hydroxyaromatic compound is subsequently sulfurized and neutralized in any order to provide a salt of a sulfurized alkyl-substituted hydroxyaromatic composition. The sulfurization and neutralization steps can be performed in any order so as to provide the salt of the sulfurized alkyl-substituted hydroxyaromatic composition. Alternatively, the neutralization and sulfurization steps can be carried out simultaneously.

In general, sulfurization is carried out by contacting the alkyl-substituted hydroxyaromatic compound with a sulfur source which introduces $S_x$ bridging groups between alkyl-substituted hydroxyaromatic compounds, wherein x is 1 to 7, in the presence of a base. Any suitable sulfur source can be used such as, for example, elemental sulfur or a halide thereof such as sulphur monochloride or sulphur dichloride, hydrogen sulfide, sulfur dioxide and sodium sulfide hydrates. The sulfur can be employed either as molten sulfur or as a solid (e.g., powder or particulate) or as a solid suspension in a compatible hydrocarbon liquid.

The base catalyzes the reaction to incorporate sulfur onto the alkylhydroxyaromatic compound. A suitable base includes, but is not limited to, NaOH, KOH, $Ca(OH)_2$ and the like and mixtures thereof.

The base is generally employed at from about 0.01 to about 1 mole percent to the alkyl-substituted hydroxyaromatic compound in the reaction system. In one embodiment, the base is employed at from about 0.01 to about 0.1 mole percent, to the alkyl-substituted hydroxyaromatic compound in the reaction system. The base can be added to the reaction mixture as a solid or a liquid. In one preferred embodiment, the base is added as an aqueous solution.

Sulfur is generally employed at from about 0.5 to about 4 moles per mole of the alkyl-substituted hydroxyaromatic compound in the reaction system. In one embodiment, sulfur is employed at from about 0.8 to 2 moles per mole of the alkyl-substituted hydroxyaromatic compound. In one embodiment, sulfur is employed at from about 1 to 1.5 moles per mole of alkyl-substituted hydroxyaromatic compound.

The temperature range in which the sulfurization reaction is carried out is generally about 150° C. to about 200° C. In one embodiment, the temperature range is from about 160° C. to about 180° C. The reaction can be conducted under atmospheric pressure (or slightly lower) or at elevated pressures. During sulfurization a significant amount of by-product hydrogen sulfide gas is evolved. In one embodiment the reaction is carried out under vacuum to facilitate the $H_2S$ elimination. The exact pressure developed during the reaction is dependent upon such factors as the design and operation of the system, the reaction temperature, and the vapor pressure of the reactants and products and it may vary during the course of the reaction. In one embodiment, the process pressures are at atmospheric to about 20 mm Hg.

Neutralization of the sulfurized or unsulfurized alkyl-substituted hydroxyaromatic compound may be carried out in a continuous or batch process by any method known to a person skilled in the art Numerous methods are known in the art to neutralize the sulfurized or unsulfurized alkyl-substituted hydroxyaromatic compounds and to produce basic phenates by Incorporation of a source of base. In general, neutralization can be carried out by contacting the sulfurized or unsulfurized alkyl-substituted hydroxyaromatic compound with a metal base under reactive conditions, preferably in an inert-compatible liquid hydrocarbon diluent. If desired, the reaction can be conducted under an inert gas, typically nitrogen. The metal base may be added either in a single addition or in a plurality of additions at intermediate points during the reaction.

Suitable metal basic compounds include hydroxides, oxides or alkoxides of the metal such as (1) an alkali metal salt derived from a metal base selected from an alkali hydroxide, alkali oxide or an alkali alkoxide, or (2) an alkaline earth metal salt derived from a metal base selected from an alkaline earth hydroxide, alkaline earth oxide or alkaline earth alkoxide. Representative examples of metal basic compounds with hydroxide functionality include lithium hydroxide, potassium hydroxide, sodium hydroxide, magnesium hydroxide, calcium hydroxide, barium hydroxide, aluminum hydroxide and the like. Representative examples of metal basic compounds with oxide functionality include lithium oxide, magnesium oxide, calcium oxide, barium oxide and the like. In one embodiment, the alkaline earth metal base is slaked lime (calcium hydroxide), because of its handling convenience and cost versus, for example, calcium oxide.

Neutralization is typically conducted in a suitable solvent or diluents oil, such as toluene, xylene and commonly with a promoter such as an alcohol, e.g., a $C_1$ to $C_{16}$ alcohol, such as methanol, decyl alcohol, or 2-ethyl hexanol; a diol, e.g., $C_2$ to $C_4$ alkylene glycols, such as ethylene glycol; and/or carboxylic acids. Suitable diluent oils include naphthenic oils and mixed oils, e.g., paraffinic oils such as 100 neutral oil. The quantity of solvent or diluent oil used is such that the amount of solvent or oil in the final product constitutes from, about 25% to about 65% by weight of the final product, preferably from about 30% to about 50%. For example, the source of alkaline earth metal is added in excess as a slurry (i.e., as a pre-mixture of source of an alkaline earth metal lime, solvent or diluent oil) and then reacted with the sulfurized or unsulfurized alkyl-substituted hydroxyaromatic compound.

The neutralization reaction between the metal base and the sulfurized or unsulfurized alkyl-substituted hydroxyaromatic compound is typically conducted at temperatures above room temperature (20° C.). In general, neutralization can be carried out at a temperature of between about 20° C. and about 150° C. it is however preferred to carry the neutralization at low temperature. In one embodiment, neutralization can be carried out at a temperature of between about 25° C. and about 30° C. The neutralization reaction itself should take place for a period of time of from about 5 to about 60 minutes. If desired, the neutralization reaction is carried out in the presence of a promoter such as ethylene glycol, formic acid, acetic acid, and the like and mixtures thereof.

Upon completion of the sulfurizing and neutralizing of the alkyl-substituted hydroxyaromatic compound, a neutral salt of a sulfurized alkyl-substituted hydroxyaromatic composition is obtained. If desired, the neural salt of a sulfurized alkyl-substituted hydroxyaromatic composition can be overbased to provide an overbased salt of a sulfurized alkyl-substituted hydroxyaromatic composition. Overbasing can be carried out either during or after one of the sulfurization and neutralization steps and by any method known by a person skilled in the art. Alternatively, sulfurization, neutralization and overbasing can be carried out simultaneously. In general, the overbasing is carried out by reaction with an acidic overbasing compound such as, for example, carbon dioxide or boric acid. In one embodiment, an overbasing process is by way of carbonation, i.e., a reaction with carbon dioxide. Such carbonation can be conveniently effected by addition of solvents: like aromatic solvents, alcohols or a polyols, typically an alkylene diol, e.g., ethylene glycol. Conveniently, the reaction is conducted by the simple expedient of bubbling gaseous carbon dioxide through the reaction mixture. Excess solvents and any water formed during the overbasing reaction can be conveniently removed by distillation either during or after the reaction.

In one embodiment, the overbasing reaction is carried out in a reactor by reacting the salt of the sulfurized alkyl-substituted hydroxyaromatic composition with a source of an alkaline earth metal such as lime (i.e., an alkaline earth metal hydroxide) in the presence of carbon dioxide, and in the presence of an aromatic solvent (e.g., xylene), and a hydrocarbyl alcohol such as methanol. Conveniently, the reaction is conducted by the simple expedient of bubbling gaseous carbon dioxide through the reaction mixture. The carbon dioxide is introduced over a period of about 1 hour to about 3 hours, at a temperature ranging from about 30° C. to about 60° C. The degree of overbasing may be controlled by the quantity of the source of an alkaline earth metal, carbon dioxide and the reactants added to the reaction mixture and the reaction conditions used during the carbonation process.

In another embodiment of the invention, the overbasing reaction can be carried out between about 140° C. and about 150° C. in the presence of a polyol, typically an alkylene diol e.g., ethylene glycol, and/or alkanols, e.g., $C_6$ to $C_{16}$ alkanols, such as decyl alcohols, 2-ethyl hexanol. Excess solvent and any water formed during the overbasing reaction can be conveniently removed by distillation either during or after the reaction.

The overbased salt of a sulfurized alkyl-substituted hydroxyaromatic composition may have a TBN of from about 50 to about 500.

In general, the resulting neutral or overbased salt of a sulfurized alkyl-substituted hydroxyaromatic composition will contain an amount, by combined mass, of unsulfurized alkyl-substituted hydroxyaromatic compound and its unsulfurized metal salt that will need to be further reduced in order minimize any potential health risks to customers and to avoid potential regulatory issues, in one embodiment, the resulting non-posted neutral or overbased salt of a sulfurized alkyl-substituted hydroxyaromatic composition will ordinarily contain from about 2 to about 10 wt. %, by combined mass, of the unsulfurized alkyl-substituted hydroxyaromatic compound and its unsulfurized metal salt.

As one skilled in the art would understand, the salt of a sulfurized alkyl-substituted hydroxyaromatic composition can contain other components in addition to the unsulfurized alkyl-substituted hydroxyaromatic compound and its unsulfurized metal salt.

In step (b), the neutral or overbased salt of a sulfurized alkyl-substituted hydroxyaromatic composition is reacted with an effective amount of an aldehyde and a primary and/or secondary monoamine compound having at least one active hydrogen and under reaction conditions sufficient, to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

Suitable aldehydes include formaldehyde, aldehydes having the formula

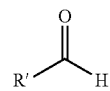

wherein R' is a branched or linear $C_1$ to $C_{10}$ alkyl radical, $C_3$ to $C_{10}$ cycloalkyl radical, $C_6$ to $C_{10}$ aryl radical, $C_7$ to $C_{20}$ alkaryl radical, or a $C_7$ to $C_{20}$ aralkyl radical, and the like and mixtures thereof. In one embodiment, the aldehyde is a non-enolizable aldehyde.

Representative examples of aliphatic aldehydes for use herein include, but are not limited to, formaldehyde, acetaldehyde, propionaldehyde, butyraldehyde, valeraldehyde, caproaldehyde, heptaldehyde and the like.

Representative examples of aromatic aldehydes for use herein include, but are not limited to, benzaldehyde, alkylbenzaldehyde such as para-tolualdehyde, hydroxybenzaldehyde and the like.

Also useful are formaldehyde producing reagents, such aqueous formaldehyde solutions such as formalin solutions, formaldehyde oligomers, e.g. trioxane, or polymers of formaldehyde, such as paraformaldehyde. In one preferred embodiment, the aldehyde is paraformaldehyde used.

In general, an effective amount of aldehyde present in step (b) ranges from about 1 molar equivalents to about 15 molar equivalents per equivalent of the unsulfurized alkyl-substituted hydroxyaromatic compound and its unsulfurized metal salt, present in the neutral or overbased salt of a sulfurized alkyl-substituted hydroxyaromatic composition. In one embodiment, the amount of aldehyde present in step (b) is from about 1 molar equivalents to about 10 equivalents per equivalent of the unsulfurized alkyl-substituted hydroxyaromatic compound and its unsulfurized metal salt present in the neutral or overbased salt of a sulfurized alkyl-substituted hydroxyaromatic composition.

Suitable amine compounds are primary or secondary monoamines having at least one active hydrogen. In one embodiment a suitable primary monoamine compound for use herein is represented by the formula $HNRR^1$, where one of the radicals R or R' is hydrogen and the other radical is a $C_1$-$C_{20}$ hydrocarbyl radical. Examples of such $C_1$-$C_{30}$ hydrocarbyl radicals include, but are not limited to, a straight or branched, substituted or unsubstituted $C_1$-$C_{30}$ alkyl radical, a substituted or unsubstituted $C_3$-$C_{30}$ cycloalkyl radical, a substituted or unsubstituted $C_3$-$C_{30}$ cycloalkylalkyl radical, a substituted or unsubstituted $C_3$-$C_{30}$ cycloalkenyl radical, a substituted or unsubstituted $C_5$-$C_{30}$ aryl radical, and a substituted or unsubstituted $C_5$-$C_{30}$ aryl alkyl radical; a substituted or unsubstituted $C_1$ to $C_{20}$ alcohol radical; a substituted or unsubstituted $C_1$ to $C_{20}$ alkoxy radical and the like.

Representative examples of alkyl radicals for use herein include, by way of example, a straight or branched alkyl chain radical containing carbon and hydrogen atoms of from 1 to about 30 carbon atoms and preferably from 1 to about 6 carbon atoms with or without unsaturation, to the rest of the molecule, e.g., methyl, ethyl, n-propyl, 1-methylethyl (iso-propyl), n-butyl, n-pentyl, etc., and the like.

Representative examples of cycloalkyl radicals for use herein include, by way of example, a substituted or unsubstituted non-aromatic mono or multicyclic ring system of about 3 to about 30 carbon atoms such as, for example, cyclopropyl, cyclobutyl, cyclopentyl, cyclohexyl, perhydronapththyl, adamantyl and norbornyl groups, bridged cyclic groups or sprirobicyclic groups, e.g., spiro-(4,4)-non-2-yl and the like.

Representative examples of cycloalkylalkyl radicals for use herein include, by way of example, a substituted or unsubstituted cyclic ring-containing radical containing from about 3 to about 30 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like.

Representative examples of cycloalkenyl radicals for use herein include, by way of example, a substituted or unsubstituted cyclic ring-containing radical containing from about 3 to about 30 carbon atoms with at least one carbon-carbon double bond such as, for example, cyclopropenyl, cyclobutenyl, cyclopentenyl and the like.

Representative examples of aryl radicals for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like.

Representative examples of arylalkyl radicals for use herein include, by way of example, a substituted or unsubstituted aryl group as defined herein directly bonded to an alkyl group as defined herein, e.g., —$CH_2C_6H_5$, —$C_2H_5C_6H_5$ and the like.

Representative examples of alcohol radicals for use herein include, by way of example, an —OH group attached via carbon linkage to the rest of the molecule, i.e., of the general formula —$R^2OH$, wherein $R^2$ is an alkyl, cycloalkyl, cycloalkylalkyl, cycloalkenyl, aryl or an arylalkyl as defined herein and the OH group is attached to any carbon atom.

Representative examples of alkoxy radicals for use herein include, by way of example, an alkyl group as defined herein attached via oxygen linkage to the rest of the molecule, i.e., of the general formula —$OR^2$, wherein $R^3$ is an alkyl, cycloalkyl, cycloalkylalkyl, cycloalkenyl, aryl or an arylalkyl as defined herein, e.g., —$OCH_3$, —$OC_2H_5$, or —$OC_6H_5$, and the like.

The substituents in the 'substituted alkyl', 'substituted cycloalkyl', 'substituted cycloalkylalkyl', 'substituted cycloalkenyl', 'substituted aryl', 'substituted arylalkyl', 'substituted alcohol', and 'substituted alkoxy' may be the same or different and include one or more substituents such as hydrogen, hydroxy, halogen, carboxyl oxo (=O), thio (=S), substituted or unsubstituted alkyl, substituted or unsubstituted alkoxy, and the like.

Suitable primary monoamine compounds of the formula $HNRR^1$ include, but are not limited to, alkylamines such as methylamine, ethylamine, n-propylamine, isopropylamine, n-butylamine, isobutylamine, sec-butylamine, tert-butylamine, pentylamine, hexylamine, heptylamine, octylamine, nonylamine, decylamine, undecylamine, dodecylamine, tetradecylamine, hexadodecylamine, stearylamine, octadecylamine, eicosylamine, and the like; cycloalkylamines such as cyclopentylamine, cyclohexylamine, and the like; arylamines such as aniline, benzyl amine, 2-aminotoluene, 3-aminotoluene, 4-aminotoluene, and the like; alkanolamines such as methanolamine, ethanolamine, and the like; alkoxyamines such as 2,4-dimethylaniline, 2,3-dimethylaniline, 2,5-dimethylaniline, 2,6-dimethylaniline, 3,4-dimethylaniline, 3,5-dimethylaniline, 2,4,5-trimethylaniline, 2,4,6-trimethylaniline, 3,4,5,6-tetramethylaniline, 2,4,5,6-tetramethylaniline, 2,3,5,6-tetramethylaniline, 2-ethyl-3-hexylaniline, 2-ethyl-4-hexylaniline, 2-ethyl-5-hexylaniline, 2-ethyl-6-hexylaniline, 3-ethyl-4-hexylaniline, 3-ethyl-5-hexylaniline, 3-ethyl-2-hexylaniline, 4-ethyl-2-hexylaniline, 5-ethyl-2-hexylaniline, 6-ethyl-2-hexylaniline, 4-ethyl-3-hexylaniline, 5-ethyl-3-hexylaniline, 3,4,6-triethyltoluene, 2-methoxyaniline, 3-methoxyaniline, 4-methoxyaniline, 2-methoxy-3-methylaniline, 2-methoxy-4-methylaniline, 2-methoxy-5-methylaniline, 2-methoxy-6-methylaniline, 3-methoxy-2-methylaniline, 3-methoxy-4-methylaniline, 3-methoxy-5-methylaniline, 3-methoxy-6-methylaniline, 4-methoxy-2-methylaniline, 4-methoxy-3-methylaniline, 2-ethoxyaniline, 3-ethoxyaniline, 4-ethoxyaniline, 4-methoxy-5-methylaniline, 4-methoxy-6-methylaniline, 2-methoxy-3-ethylaniline, 2-methoxy-4-ethylaniline, 2-methoxy-5-ethylaniline, 2-methoxy-6-ethylaniline, 3-methoxy-2-ethylaniline, 3-methoxy-4-ethylaniline, 3-methoxy-5-ethylaniline, 3-methoxy-6-ethylaniline, 4-methoxy-2-ethylaniline, 4-methoxy-3-ethylaniline, 2-methoxy-2,3,4-trimethylaniline, 3-methoxy-2,4,5-trimethylaniline, 4-methoxy-2,3,5-trimethylaniline, and the like and mixtures thereof.

In another embodiment, a suitable secondary monoamine compound for use herein is represented by the formula $HNRR^1$, where R and $R^1$ are the same or different and are $C_1$-$C_{30}$ hydrocarbyl radicals. Examples of such hydrocarbyl radicals for R and $R^1$ of the secondary monoamine compound can be any of the hydrocarbyl radicals discussed above for the primary monoamine compounds. Suitable secondary monoamine compounds of the formula $HNRR^1$ include, but are not limited to, dialkylamines such as dimethylamine, diethylamine, methylethylamine, di-n-propylamine, diisopropylamine, diisobutylamine, di-sec-butylamine, di-tert-butylamine, dipentylamine, dihexylamine, and the like, dicycloamines such as dicyclopentylamine, dicyclohexylamine, and the like; diarylamines such as diphenylamine, and the like; dialkanolamines such as diethanolamine, di-n-propanolamine, diisopropanolamine, and the like. N-alkylalkanolamines such as N-methylethanolamine, N-ethylethanolamine and the like and mixtures thereof.

In general, an effective amount of the monoamine compound present in step (b) ranges from about 1 molar equivalents to about 15 equivalents per equivalent of the unsulfurized alkyl-substituted hydroxyaromatic compound and its unsulfurized metal salt present in the neutral or overbased salt of a sulfurized alkyl-substituted hydroxyaromatic composition. In one embodiment, the amount of monoamine compound present in step (b) is from about 1 molar equivalents to about 10 equivalents per equivalent, of the unsulfurized alkyl-substituted hydroxyaromatic compound and its unsulfurized metal salt present in the neutral or overbased salt of a sulfurized alkyl-substituted hydroxyaromatic composition.

In one embodiment, an effective amount of aldehyde and the monoamine compound present in step (b) is a molar ratio of aldehyde to the monoamine compound ranging from about 1:1 to about 5:1.

In one embodiment, the reaction is carried out employing a molar ratio of the neutral or overbased salt of a sulfurized alkyl-substituted hydroxyaromatic composition to aldehyde to monoamine compound ranging from about 1:1:1 to about 1:10:10.

As one skilled in the art will readily appreciate, the reaction conditions will necessarily depend on the reactants employed and their respective effective amount. In one embodiment, suitable reaction conditions include a temperature ranging from about 70° C. to about 180° C. and time period for the reaction ranging from about 30 minutes to about 14 hour.

If desired, step (b) can be carried out in the presence of a suitable solvent, which can be recovered from the reaction product. Suitable solvents include organic solvents such as, for example, aromatic hydrocarbon solvents such as toluene, benzene, and the like, alcohol solvents such as methanol, ethanol, decylalcohol, 2-ethyl hexanol and the like, and mixtures thereof. If desired, the reaction may be carried out in a mineral lubricating oil and the resulting product is recovered as a lubricating oil concentrate.

The reaction of the neutral or overbased salt of a sulfurized alkyl-substituted hydroxyaromatic composition with an effective amount of aldehyde and primary and/or secondary monoamine compound having at least one active hydrogen is carried out under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition. In one embodiment, the reaction of the neutral or overbased salt of a sulfurized alkyl-substituted hydroxyaromatic composition with an effective amount of aldehyde and primary and/or secondary monoamine compound having at least one active hydrogen is carried out under reaction conditions sufficient to provide a post-treated salt of the sulfurized alkyl-substituted hydroxyaromatic composition having at least about 75% reduced content, by combined mass, of the unsulfurized alkyl-substituted hydroxyaromatic compound and its unsulfurized metal salt.

In one embodiment, the reaction of the neutral or overbased salt of a sulfurized alkyl-substituted hydroxyaromatic composition with an effective amount of aldehyde and primary and/or secondary monoamine compound having at least one active hydrogen is carried out under reaction conditions sufficient to provide a post-treated salt of the sulfurized alkyl-substituted hydroxyaromatic composition having at least about 80% reduced content, by combined mass, of the unsulfurized alkyl-substituted hydroxyaromatic compound and its unsulfurized metal salt. In one embodiment, the reaction of the neutral or overbased salt of a sulfurized alkyl-substituted hydroxyaromatic composition with an effective amount of aldehyde and primary and/or secondary monoamine compound having at least one active hydrogen is carried out under reaction conditions sufficient to provide a post-treated salt of the sulfurized alkyl-substituted hydroxyaromatic composition having at least about 85% reduced content, by combined mass, of the unsulfurized alkyl-substituted hydroxyaromatic compound and its unsulfurized metal salt.

In one embodiment, the reaction of the neutral or overbased salt of a sulfurized alkyl-substituted hydroxyaromatic composition with an effective amount of aldehyde and primary and/or secondary monoamine compound having at least one active hydrogen is carried out under reaction conditions sufficient to provide a post-treated salt of the sulfurized alkyl-substituted hydroxyaromatic composition having at least about 90% reduced content, by combined mass, of the unsulfurized alkyl-substituted hydroxyaromatic compound and its unsulfurized metal salt. In one embodiment, the reaction of the neutral or overbased salt of a sulfurized alkyl-substituted hydroxyaromatic composition with an effective amount, of aldehyde and primary and/or secondary monoamine compound having at least one active hydrogen is carried out under reaction conditions sufficient to provide a post-treated salt of the sulfurized alkyl-substituted hydroxyaromatic composition having at least about 95% reduced content, by combined mass, of the unsulfurized alkyl-substituted hydroxyaromatic compound and its unsulfurized metal salt. In one embodiment, the reaction of the neutral or overbased salt of a sulfurized alkyl-substituted hydroxyaromatic composition with an effective amount of aldehyde and primary and/or secondary monoamine compound having at least one active hydrogen is carried out under reaction conditions sufficient to provide a post-treated salt of the sulfurized alkyl-substituted hydroxyaromatic composition having 100% reduced content, by combined mass, of the unsulfurized alkyl-substituted hydroxyaromatic compound and its unsulfurized metal salt.

Lubricating Oil Composition

Another embodiment of the present invention is directed to a lubricating oil composition containing at least (a) a major amount of an oil of lubricating viscosity; and (b) at least one post-treated salt of a sulfurized alkyl-substituted hydroxyaromatic composition which is a reaction product of (i) a salt of a sulfurized alkyl-substituted hydroxyaromatic composition, wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof, (ii) a source of an aldehyde and (iii) a primary and/or secondary monoamine compound having at least one active hydrogen.

Another embodiment of the present invention is directed to a lubricating oil composition containing at least (a) a major amount of an oil of lubricating viscosity; and (b) at least one post-treated salt of a sulfurized alkyl-substituted hydroxyaromatic composition having a reduced content, by combined mass, of an unsulfurized alkyl-substituted hydroxyaromatic compound and its unsulfurized metal salt, the post-treated salt of a sulfurized alkylhydroxyaromatic composition being produced by a process comprising:

(i) providing a salt of a sulfurized alkyl-substituted hydroxyaromatic composition containing an unsulfurized alkyl-substituted hydroxyaromatic compound and its unsulfurized metal salt; wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof; and (ii) reacting the salt of a sulfurized alkyl-substituted hydroxyaromatic composition with an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

Generally, a post-treated salt of the sulfurized alkyl-substituted hydroxyaromatic composition, of this invention will be present in the lubricating oil compositions in an amount of about amount of about 0.01 to about 10 wt %, based on the total weight of the lubricating oil composition. In one embodiment, a post-treated salt of the sulfurized alkyl-substituted hydroxyaromatic composition of this invention will be present in the lubricating oil compositions in an amount of about amount of about 0.01 to about 3 wt. %, based on the total weight of the lubricating oil composition.

The oil of lubricating viscosity for use in the lubricating oil compositions of this invention, also referred to as a base oil, is typically present in a major amount, e.g., an amount of greater than 50 wt. %, or greater than about 70 wt. %, or from about 80 to about 99.5 wt. % or from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (° C.). Generally, individually the base oils used as engine oils will have a kinematic viscosity range at 100° C. of about 2 cSt to about 30 cSt, or from about 3 cSt to about 16 cSt, or from about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C. The kinematic viscosity of the base oils or the lubricating oil compositions disclosed herein can be measured according to ASTM D 445, which is incorporated herein by reference.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th. Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl, alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaetythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphonic acid, etc, polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been, further treated in one or more purification steps to improve one or more properties. These purification, techniques are known to those of skill in the art and include, for example, solvent extractions, secondary distillation, acid or base extraction, filtration, percolation, hydrotreating, de-waxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products, Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil compositions of the present invention may also contain other conventional additives that can impart or improve any desirable property of the lubricating oil composition in which these additives are dispersed or dissolved. Any additive known to a person of ordinary skill in the art may be used in the lubricating oil compositions disclosed herein. Some suitable additives have been described in Mortier et al., "Chemistry and Technology of Lubricants," 2nd Edition, London, Springer, (1996); and Leslie R. Rudnick, "Lubricant Additives; Chemistry and Applications." New York, Marcel Dekker (2003), both of which are incorporated herein by reference. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

In general, the concentration of each of the additives in the lubricating oil composition, when used, may range from about 0.001 wt. % to about 10 wt. %, from about 0.01 wt. % to about 5 wt. %, or from about 0.1 wt. % to about 2.5 wt. %, based, on the total weight of the lubricating oil composition. Further, the total amount of the additives in the lubricating oil composition may range from about 0.001 wt. % to about 20 wt. %, from about 0.01 wt % to about 10 wt. %, or from about 0.1 wt % to about 5 wt. %, based on the total weight of the lubricating oil composition.

The lubricating oil composition disclosed herein can contain one or more antioxidants that can reduce or prevent the oxidation of the base oil. Any antioxidant known by a person of ordinary skill in the art may be used in the lubricating oil composition. Non-limiting examples of suitable antioxidants include amine-based antioxidants (e.g., alkyl diphenylamines such as bis-nonylated diphenylamine, bis-octylated diphenylamine, and octylated/butylated diphenylamine, phenyl-$\alpha$-naphthylamine, alkyl or arylalkyl substituted phenyl-$\alpha$-naphthylamine, alkylated p-phenylene diamines, tetramethyl-diaminodiphenylamine and the like), phenolic antioxidants (e.g., 2-tert-butylphenol, 4-methyl-2,6-di-tert-butylphenol, 2,4,6-tri-tert-butylphenol, 2,6-di-tert-butyl-p-cresol, 2,6-di-tert-butylphenol, 4,4'-methylenebis-(2,6-di-tert-butylphenol), 4,4'-thiobis(6-di-tert-butyl-o-cresol) and the like), sulfur-based antioxidants (e.g., dilauryl-3,3'-thiodipropionate, sulfurized phenolic antioxidants and the like), phosphorous-based antioxidants (e.g., phosphites and the like), zinc dithiophosphate, oil-soluble copper compounds and combinations thereof. The amount of the antioxidant may vary from about 0.01 wt. % to about 10 wt. %, from about 0.05 wt. % to about 5 wt. %, or from about 0.1 wt. % to about 3 wt. %, based on the total weight of the lubricating oil composition. Some suitable antioxidants have been described in Leslie R. Rudnick, "Lubricant Additives: Chemistry and Applications," New York, Marcel Dekker, Chapter 1, pages 1-28 (2003), which is incorporated herein, by reference.

The lubricating oil composition disclosed herein can contain one or more ashless dispersant compounds to maintain in suspension insoluble materials resulting from oxidation during use, thus preventing sludge flocculation and precipitation or deposition on metal parts. Dispersants may also function to reduce changes in lubricating oil viscosity by preventing the growth of large contaminant particles in the lubricant. Any dispersant known by a person of ordinary skill in the art may be used in the lubricating oil composition. An ashless dispersant generally comprises an oil soluble polymeric hydrocarbon backbone having functional groups that are capable of associating with particles to be dispersed.

In one embodiment, an ashless dispersant is one or more basic nitrogen-containing ashless dispersants. Nitrogen-containing basic ashless (metal-free) dispersants contribute to the base number or BN (as can be measured by ASTM D 2896-11) of a lubricating oil composition to which they are added, without introducing additional sulfated ash. Basic nitrogen-containing ashless dispersants useful in this invention include hydrocarbyl succinimides; hydrocarbyl succinamides; mixed ester/amides of hydrocarbyl-substituted succinic acids formed by reacting a hydrocarbyl-substituted succinic acylating agent stepwise or with a mixture of alcohols and amines, and/or with amino alcohols; Mannich condensation products of hydrocarbyl-substituted phenols, formaldehyde and polyamines; and amine dispersants formed by reacting high molecular weight aliphatic or alicyclic halides with amines, such as polyalkylene polyamines. Mixtures of such dispersants can also be used.

Representative examples of ashless dispersants include, but are not limited to, amines, alcohols, amides, or ester polar moieties attached to the polymer backbones via bridging groups. An ashless dispersant may be, for example, selected from oil soluble salts, esters, amino-esters, amides, imides, and oxazolines of long chain hydrocarbon substituted mono and dicarboxylic acids or their anhydrides; thiocarboxylate derivatives of long chain hydrocarbons, long chain aliphatic hydrocarbons having a polyamine attached directly thereto; and Mannich condensation products formed by condensing a long chain substituted phenol with formaldehyde and polyalkylene polyamine.

Carboxylic dispersants are reaction products of carboxylic acylating agents (acids, anhydrides, esters, etc.) comprising at least about 34 and preferably at least about 54 carbon atoms with nitrogen containing compounds (such as amines), organic hydroxy compounds (such as aliphatic compounds including monohydric and polyhydric alcohols, or aromatic compounds including phenols and naphthols), and/or basic inorganic materials. These reaction products include imides, amides, and esters.

Succinimide dispersants are a type of carboxylic dispersant. They are produced by reacting hydrocarbyl-substituted succinic acylating agent with organic hydroxy compounds, or with amines comprising at least one hydrogen atom attached to a nitrogen atom, or with a mixture of the hydroxy compounds and amines. The term "succinic acylating agent" refers to a hydrocarbon-substituted succinic acid or a succinic acid-producing compound, the latter encompasses the acid itself. Such materials typically include hydrocarbyl-substituted succinic acids, anhydrides, esters (including half esters) and halides.

Succinic-based dispersants have a wide variety of chemical structures. One class of succinic-based dispersants may be represented by the formula:

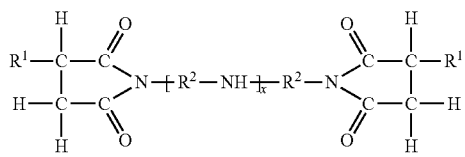

wherein each $R^1$ is independently a hydrocarbyl group, such as a polyolefin-derived group. Typically the hydrocarbyl group is an alkyl group, such as a polyisobutyl group. Alternatively expressed, the $R^1$ groups can contain about 40 to about 500 carbon atoms, and these atoms may be present in aliphatic forms. $R^2$ is an alkylene group, commonly an ethylene ($C_2H_4$) group. Examples of succinimide dispersants include those described in, for example, U.S. Pat. Nos. 3,172,892, 4,234,435 and 6,165,235.

The polyalkenes from which the substituent groups are derived are typically homopolymers and interpolymers of polymerizable olefin monomers of 2 to about 16 carbon atoms, and usually 2 to 6 carbon atoms. The amines which are reacted with the succinic acylating agents to form the carboxylic dispersant composition can be monoamines or polyamines.

Succinimide dispersants are referred to as such since they normally contain nitrogen largely in the form of imide functionality, although the amide functionality may be in the form of amine salts, amides, imidazolines as well as mixtures thereof. To prepare a succinimide dispersant, one or more succinic acid-producing compounds and one or more amines are heated and typically water is removed, optionally in the presence of a substantially inert organic liquid solvent/diluent. The reaction temperature can range from about 80° C. up to the decomposition temperature of the mixture or the product, which typically falls between about 100° C. to about 300° C. Additional details and examples of procedures for preparing the succinimide dispersants of the present invention include those described in, for example, U.S. Pat. Nos. 3,172,892, 3,219,666, 3,272,746, 4,234,435, 6,165,235 and 6,440,905.

Suitable ashless dispersants may also include amine dispersants, which are reaction products of relatively high molecular weight aliphatic halides and amines, preferably polyalkylene polyamines. Examples of such amine dispersants include those described in, for example, U.S. Pat. Nos. 3,275,554, 3,438,757, 3,454,555 and 3,565,804.

Suitable ashless dispersants may further include "Mannich dispersants," which are reaction products of alkyl phenols in which the alkyl group contains at least about 30 carbon atoms with aldehydes (especially formaldehyde) and amines (especially polyalkylene polyamines). Examples of such dispersants include those described in, for example, U.S. Pat. Nos. 3,036,003, 3,586,629, 3,591,598 and 3,980,569.

Suitable ashless dispersants may also be post-treated ashless dispersants such as post-treated succinimides, e.g., post-treatment processes involving borate or ethylene carbonate as disclosed in, for example, U.S. Pat. Nos. 4,612,132 and 4,746,446; and the like as well as other post-treatment processes. The carbonate-treated alkenyl succinimide is a polybutene succinimide derived from polybutenes having a molecular weight of about 450 to about 3000, preferably from about 900 to about 2500, more preferably from about 1300 to about 2400, and most preferably from about 2000 to about 2400, as well as mixtures of these molecular weights. Preferably, it is prepared by reacting, under reactive conditions, a mixture of a polybutene succinic acid derivative, an unsaturated acidic reagent copolymer of an unsaturated acidic reagent and an olefin, and a polyamine, such as disclosed in U.S. Pat. No. 5,716,912, the contents of which are incorporated herein by reference.

Suitable ashless dispersants may also be polymeric, which are interpolymers of oil-solubilizing monomers such as decyl methacrylate, vinyl decyl ether and high molecular weight olefins with monomers containing polar substitutes. Examples of polymeric dispersants include those described in, for example, U.S. Pat. Nos. 3,329,658; 3,449,250 and 3,666,730.

In one preferred embodiment of the present invention, an ashless dispersant for use in the lubricating oil composition is a bis-succinimide derived from a polyisobutenyl group having a number average molecular weight of about 700 to about 2300. The dispersant(s) for use in the lubricating oil compositions of the present invention are preferably non-polymeric (e.g., are mono- or bis-succinimides).

The lubricating oil composition disclosed herein can contain an additional detergent. Any compound or a mixture of compounds that can reduce or slow the build up of engine deposits can be used as a detergent. Non-limiting examples of suitable metal detergent include sulfurized or unsulfurized alkyl or alkenyl phenates, alkyl or alkenyl aromatic sulfonates, borated sulfonates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multiacid, and chemical and physical mixtures thereof. Other non-limiting examples of suitable metal detergents include metal sulfonates, salicylates, phosphonates, thiophosphonates and combinations thereof. The metal can be any metal suitable for making sulfonate, salicylate or phosphonate detergents. Non-limiting examples of suitable metals include alkali metals, alkaline metals and transition metals. In some embodiments, the metal is Ca, Mg, Ba, K, Na, Li or the like.

Generally, the amount of the detergent additive can be less than 10,000 ppm, less than 1000 ppm, less than 100 ppm, or less than 10 ppm, based, on the total weight of the lubricating oil composition. In some embodiments, the amount of the detergent is from about 0.001 wt. % to about 5 wt. %, from about 0.05 wt. % to about 3 wt. %, or from about 0.1 wt. % to about 1 wt. %, based on the total weight of the lubricating oil composition. Some suitable detergents have been described in Mortier et al., "Chemistry and Technology of Lubricants," 2nd Edition, London, Springer, Chapter 3, pages 75-85 (1996); and Leslie R. Rudnick, "Lubricant Additives: Chemistry and Applications," New York, Marcel Dekker, Chapter 4, pages 113-136 (2003), both of which are incorporated herein, by reference.

The lubricating oil composition disclosed herein can contain one or more friction modifiers that can lower the friction between moving parts. Any friction modifier known by a person of ordinary skill in the art may be used in the lubricating oil composition. Non-limiting examples of suitable friction modifiers include fatty carboxylic acids; derivatives (e.g., alcohol, esters, borated esters, amides, metal salts and the like) of fatty carboxylic acid; mono-, di- or tri-alkyl substituted phosphoric acids or phosphonic acids; derivatives (e.g., esters, amides, metal salts and the like) of mono-, di- or tri-alkyl substituted phosphoric acids or phosphonic acids; mono-, di- or tri-alkyl substituted amines; mono- or di-alkyl substituted amides and combinations thereof. In some embodiments examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, or a $C_6$ to $C_{24}$, or a $C_6$ to $C_{20}$, fatty acid ester and a nitrogen-containing compound selected from the group consisting of ammonia, and an alkanolamine and the like and mixtures thereof. The amount, of the friction modifier may vary from, about 0.01 wt. % to about 10 wt. %, from, about 0.05 wt. % to about 5 wt. %, or from about 0.1 wt. % to about 3 wt. %, based on the total weight of the lubricating oil composition. Some suitable friction modifiers have been described in Mortier et al., "Chemistry and Technology of Lubricants," 2nd Edition, London, Springer, Chapter 6, pages 183-187 (1996); and Leslie R. Rudnick, "Lubricant Additives: Chemistry and Applications," New York, Marcel Dekker, Chapters 6 and 7, pages 171-222 (2003), both of which are incorporated herein by reference.

The lubricating oil composition disclosed herein can contain one or more anti-wear agents that can reduce friction and excessive wear. Any anti-wear agent known by a person of ordinary skill in the art may be used in the lubricating oil composition. Non-limiting examples of suitable anti-wear agents include zinc dithiophosphate, metal (e.g., Pb, Sb, Mo and the like) salts of dithiophosphates, metal (e.g., Zn, Pb, Sb, Mo and the like) salts of dithiocarbamates, metal (e.g., Zn, Pb, Sb and the like) salts of fatty acids, boron compounds, phosphate esters, phosphite esters, amine salts of phosphoric acid esters or thiophosphoric acid esters, reaction products of dicyclopentadiene and thiophosphoric acids and combinations thereof. The amount of the anti-wear agent may vary from about 0.01 wt. % to about 5 wt. %, from about 0.05 wt. % to about 3 wt. %, or from about 0.1 wt. % to about 1 wt. %, based on the total weight of the lubricating oil composition. Some suitable anti-wear agents have been described in Leslie R. Rudnick, "Lubricant Additives: Chemistry and Applications," New York, Marcel Dekker, Chapter 8, pages 223-258 (2003), which is incorporated herein by reference.

In certain embodiments, the anti-wear agent is or comprises a dihydrocarbyl dithiophosphate metal salt, such as zinc dialkyl dithiophosphate compounds. The metal of the dihydrocarbyl dithiophosphate metal salt may be an alkali or alkaline earth metal, or aluminum, lead, tin, molybdenum, manganese, nickel or copper. In some embodiments, the metal is zinc. In other embodiments, the alkyl group of the dihydrocarbyl dithiophosphate metal salt has from about 3 to about 22 carbon atoms, from, about 3 to about 18 carbon, atoms, from about 3 to about 12 carbon atoms, or from about 3 to about 8 carbon atoms. In further embodiments, the alkyl group is linear or branched.

The amount of the dihydrocarbyl dithiophosphate metal salt including the zinc dialkyl dithiophosphate salts in the lubricating oil composition disclosed herein, is measured by its phosphorus content, in some embodiments, the phosphorus content of the lubricating oil composition disclosed herein is from about 0.01 wt. % to about 0.12 wt. %, from about 0.1 wt. % to about 0.10 wt. %, or from about 0.2 wt. % to about 0.8 wt. %, based on the total weight of the lubricating oil composition.

The lubricating oil composition disclosed herein can contain one or more foam inhibitors or anti-foam inhibitors that can break up foams in oils. Any foam inhibitor or anti-foam known by a person of ordinary skill in the art may be used in the lubricating oil composition. Non-limiting examples of suitable foam inhibitors or anti-foam inhibitors include silicone oils or polydimethylsiloxanes, fluorasilicones, alkoxylated aliphatic acids, polyethers (e.g., polyethylene glycols), branched polyvinyl ethers, alkyl acrylate polymers, alkyl methacrylate polymers, polyalkoxyamines and combinations thereof. In some embodiments, the foam inhibitors or anti-foam inhibitors comprises glycerol monostearate, polyglycol palmitate, a trialkyl monothiophosphate, an ester of sulfonated ricinoleic acid, benzoylacetone, methyl salicylate, glycerol monooleate, or glycerol dioleate. The amount of the foam inhibitors or anti-foam inhibitors may vary from about 0.01 wt. % to about 5 wt. %, from about 0.05 wt. % to about 3 wt. %, or from about 0.1 wt. % to about 1 wt. %, based on the total weight of the lubricating oil composition. Some suitable foam Inhibitors or anti-foam inhibitors have been described in Mortier et al., "Chemistry and Technology of Lubricants," 2nd Edition, London, Springer, Chapter 6, pages 190-193 (1996), which is incorporated herein by reference.

The lubricating oil composition disclosed herein can contain one or more pour point depressants that can lower the pour point of the lubricating oil composition. Any pour point depressant known by a person of ordinary skill in the art may be used in the lubricating oil composition. Non-limiting examples of suitable pour point depressants include polymethacrylates, alkyl acrylate polymers, alkyl methacrylate polymers, di(tetra-paraffin phenol)phthalate, condensates of tetra-paraffin phenol, condensates of a chlorinated paraffin with naphthalene and combinations thereof. In some embodiments, the pour point depressant comprises an ethylene-vinyl acetate copolymer, a condensate of chlorinated paraffin and phenol, polyalkyl styrene or the like. The amount of the pour point depressant, may vary from, about 0.01 wt. % to about 10 wt. %, from about 0.05 wt. % to about 5 wt. %, or from about 0.1 wt. % to about 3 wt. %, based on the total weight of the lubricating oil composition. Some suitable pour point depressants have been described in Mortier et al., "Chemistry and Technology of Lubricants," 2nd Edition, London, Springer, Chapter 6, pages 187-189 (1996); and Leslie R. Rudnick, "Lubricant Additives: Chemistry and Applications," New York, Marcel Dekker, Chapter 11, pages 329-354 (2003), both of which are incorporated herein by reference.

The lubricating oil composition disclosed herein can contain one or more demulsifiers that can promote oil-water separation in lubricating oil compositions that are exposed to water or steam. Any demulsifier known by a person of ordinary skill in the art may be used in the lubricating oil composition. Non-limiting examples of suitable demulsifiers include anionic surfactants (e.g., alkyl-naphthalene sulfonates, alkyl benzene sulfonates and the like), nonionic alkoxylated alkyl phenol resins, polymers of alkylene oxides (e.g., polyethylene oxide, polypropylene oxide, block copolymers of ethylene oxide, propylene oxide and the like), esters of oil soluble acids, polyoxyethylene sorbitan ester and combinations thereof. The amount of the demulsifier may vary from about 0.01 wt. % to about 10 wt, %, from about 0.05 wt, % to about 5 wt. %, or from about 0.1 wt. % to about 3 wt. %, based on the total weight of the lubricating oil composition. Some suitable demulsifiers have been described in Mortier et al., "Chemistry and Technology of Lubricants," 2nd Edition, London, Springer, Chapter 6, pages 190-193 (1996), which is incorporated herein by reference.

The lubricating oil composition disclosed herein can contain one or more corrosion inhibitors that can reduce corrosion. Any corrosion inhibitor known by a person of ordinary skill in the art may be used in the lubricating oil composition. Non-limiting examples of suitable corrosion inhibitor include half esters or amides of dodecylsuccinic acid, phosphate esters, thiophosphates, alkyl imidazolines, sarcosines and combinations thereof. The amount of the corrosion inhibitor may vary from about 0.01 wt. % to about 5 wt. %, from about 0.05 wt. % to about 3 wt. %, or from about 0.1 wt. % to about 1 wt. %, based on the total weight of the lubricating oil composition. Some suitable corrosion inhibitors have been described in Mortier et al., "Chemistry and Technology of Lubricants," 2nd Edition, London, Springer, Chapter 6, pages 193-196 (1996), which is incorporated herein by reference.

The lubricating oil composition, disclosed herein can contain one or more extreme pressure (EP) agents that can prevent sliding metal surfaces from seizing under conditions of extreme pressure. Any extreme pressure agent known by a person of ordinary skill in the art may be used in the lubricating oil composition. Generally, the extreme pressure agent is a compound that can combine chemically with a metal to form a surface film that prevents the welding of asperities in opposing metal surfaces under high loads. Non-limiting examples of suitable extreme pressure agents include sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefins, co-sulfurized blends of fatty acid, fatty acid ester and alpha-olefin, functionally-substituted dihydrocarbyl polysulfides, thia-aldehydes, thia-ketones, epithio compounds, sulfur-containing acetal derivatives, co-sulfurized blends of terpene and acyclic olefins, and polysulfide olefin products, amine salts of phosphoric acid esters or thiophosphoric acid esters and combinations thereof. The amount of the extreme pressure agent may vary from about 0.01 wt. % to about 5 wt. %, from about 0.05 wt. % to about 3 wt. %, or from about 0.1 wt. % to about 1 wt. %, based on the total weight of the lubricating oil composition. Some suitable extreme pressure agents have been described in Leslie R. Rudnick, "Lubricant Additives: Chemistry and Applications," New York, Marcel Dekker, Chapter 8, pages 223-258 (2003), which is incorporated herein, by reference.

The lubricating oil composition disclosed herein can contain one or more rust, inhibitors that can inhibit the corrosion of ferrous metal surfaces. Any rust inhibitor known by a person of ordinary skill in the art may be used in the lubricating oil composition. Non-limiting examples of suitable rust inhibitors include nonionic polyoxyalkylene agents, e.g., polyoxyethylene lauryl ether, polyoxyethylene higher alcohol ether, polyoxyethylene nonylphenylether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof. The amount of the rust inhibitor may vary from about 0.01 wt. % to about 10 wt. %, from about 0.05 wt. % to about 5 wt. %, or from about 0.1 wt. % to about 3 wt. %, based on the total weight of the lubricating oil composition.

The lubricating oil composition disclosed herein can contain one or more multifunctional additives. Non-limiting examples of suitable multifunctional additives include sulfurized oxymolybdenum dithiocarbamate, sulfurized oxymolybdenum organophosphorodithioate, oxymolybdenum monoglyceride, oxymolybdenum diethylate amide, amine-molybdenum complex compound, and sulfur-containing molybdenum complex compound.

The lubricating oil composition, disclosed herein can contain one or more viscosity index improvers. Non-limiting examples of suitable viscosity index improvers include polymethacrylate type polymers, ethylene-propylene copolymers, styrene-isoprene copolymers, hydrated styrene-isoprene copolymers, polyisobutylene, and dispersant type viscosity index improvers.

The lubricating oil composition disclosed herein can contain one or more metal deactivators. Non-limiting examples of suitable metal deactivators include disalicylidene propylenediamine, triazole derivatives, thiadiazole derivatives, and mercaptobenzimidazoles.

If desired, the lubricant additives may be provided as an additive package or concentrate in which the additives are incorporated into a substantially inert, normally liquid organic diluent such as, for example, mineral oil, naphtha, benzene, toluene or xylene to form an additive concentrate. These concentrates usually contain from, about 20% to about 80% by weight of such diluent. Typically, a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will typically contain one or more of the various additives, referred to above, in the desired amounts and ratios to facilitate direct combination with the requisite amount of the oil of lubricating viscosity.

In the present invention, the sulfated ash content of the total lubricating oil composition is less than 5 wt. %, less than 4 wt. %, less than 3 wt. %, less than 2 wt. %, or less than 1 wt. %, as measured according to ASTM D874-07.

The lubricating oil composition disclosed herein may be suitable for use as motor oils (or engine oils or crankcase oils), trunk piston engine oils, marine oils, transmission fluids, gear oils, power steering fluids, shock absorber fluids, brake fluids, hydraulic fluids and/or greases.

In one embodiment, the lubricating oil composition disclosed herein is a motor or engine oil. Such a motor oil composition may be used to lubricate all major moving parts in any reciprocating internal combustion engine, reciprocating compressors and in steam engines of crankcase design. In automotive applications, the motor oil composition may also be used to cool hot engine parts, keep the engine free of rust and deposits, and seal the rings and valves against leakage of combustion gases. The motor oil composition may comprise a base oil, a post-treated salt of a sulfurized alkyl-substituted hydroxyaromatic composition disclosed herein, and one or more optional additives.

In one embodiment, the lubricating oil composition disclosed herein is a gear oil for either automotive or industrial applications. The gear oil composition may be used to lubricate gears, rear axles, automotive transmissions, final drive axles, accessories in agricultural and construction equipment, gear housings and enclosed chain drives. The gear oil composition may comprise a base oil, a post-treated salt of a sulfurized alkyl-substituted hydroxyaromatic composition disclosed herein, and one or more optional additives In one embodiment, the lubricating oil composition disclosed herein is a transmission fluid. The transmission fluid composition may be used in either automatic transmission or manual transmission to reduce transmission losses. The transmission fluid composition may comprise a base oil, a post-treated salt of a sulfurized alkyl-substituted hydroxyaromatic composition disclosed herein, and one or more optional additives.

In one embodiment, the lubricating oil composition disclosed herein is a grease used in various applications where extended lubrication is required and where oil would not be retained, e.g., on a vertical shaft. The grease composition may comprise a base oil, a post-treated salt of a sulfurized alkyl-substituted hydroxyaromatic composition disclosed herein, one or more optional additives and a thickener.

The following non-limiting examples are illustrative of the present invention.

The concentration of free unsulfurized alkyl-substituted hydroxyaromatic compound and its unsulfurized metal salts in the post-treated salt of the sulfurized alkyl-substituted hydroxyaromatic composition as disclosed herein and exemplified below, as well as lubricants and oil additives containing salts of the sulfurized alkyl-substituted hydroxyaromatic composition is determined by reverse phase High Performance liquid Chromatography (HPLC). In the HPLC method, samples were prepared for analysis by weighing accurately 80 to 120 mg of sample into a 10 ml volumetric flask, diluting to the level mark with methylene chloride, and mixing until the sample is fully dissolved.

The HPLC system used in the HPLC method included a HPLC pump, a thermostatted HPLC column compartment, HPLC fluorescence detector, and PC-based chromatography data acquisition system. The particular system described is based on an Agilent 1200 HPLC with ChemStation software. The HPLC column was a Phenomenex Luna C8(2) 150×4.6 mm 5 μm 100 Å, P/N 00F4249E0.

The following system settings were used in performing the analyses:

Pump flow=1.0 ml/min
Maximum pressure=200 bars
Fluorescence wavelength: 225 excitation 313 emission: Gain=9
Column Thermostat temperature=25° C.
Injection Size=1 μL of diluted sample
Elution type: Gradient, reverse phase
Gradient: 0-7 min 85/15 methanol/water switching to 100% methanol linear Gradient.
Runtime: 17 minutes The resulting chromatograph typically contains several peaks. Peaks due to the free unsulfurized alkyl-substituted hydroxyaromatic compound and its unsulfurized metal salts, which convert to free un-sulfurized hydroxyaromatic compound under these conditions, elate together at early retention times; whereas peaks due to sulfurized salts of alkyl-substituted hydroxyaromatic compositions typically elute at longer retention times. For purposes of quantitation, the area of the single largest peak of the free unsulfurized alkyl-substituted hydroxyaromatic compound and its unsulfurized metal, salts was measured, and then that area was used to determine the concentration of the total free unsulfurized alkyl-substituted hydroxyaromatic compound and its unsulfurized metal salt species. The assumption is that the speciation of alkyl-substituted hydroxyaromatic compounds does not change; if something does change the speciation of the alkyl-substituted hydroxyaromatic compounds, then recalibration is necessary.

The area of the chosen peak Is compared to a calibration curve to arrive at the wt-% of free alkylphenol and free unsulfurized salts of alkylphenols. The calibration curve was developed using the same peak in the chromatograph obtained for the free unsulfurized alkylhydroxyaromatic compound used to make the phenate product.

EXAMPLE 1

Preparation of Mannich Post-Treated Sulfurized Calcium Phenate Composition 10 g of an overbased sulfurized calcium phenate composition (commercially available from Chevron Oronite Company LLC) having a TPP content of about 8 wt. % was heated to about 80° C. and transferred to a 100 ml two-neck round bottom flask. The temperature in the flask was maintained at about 80° C. while 5 ml of toluene solvent, (approximately 50 wt. % equivalent of the phenate charge) was added to the composition. Immediately after the addition of solvent, 5 molar equivalents of paraformaldehyde (based on molar equivalent of residual TPP) was added and then the mixture was held at 80° C. for 10 minutes. Next, 5 molar equivalents of diethylamine (based on molar equivalent of residual TPP) was then slowly added and the reaction conditions were maintained at a temperature of 80° C. for a reaction time of 4 hours. At the end of the reaction time, the solvent was distilled under vacuum. The distilled product had a residual total TPP content of 0.53 wt. %, which resulted in a 93.38% reduction.

EXAMPLES 2 TO 14 AND COMPARATIVE EXAMPLES A AND B

The following examples were repeated in substantially the same manner as Example 1 using the reactants and reaction conditions as set forth below in Table 1. In Example 5, the overbased sulfurized calcium phenate composition was first quenched with 1 molar equivalent of acetic acid prior to the addition of the Mannich reagents. For the following examples, the source of formaldehyde was paraformaldehyde and the starting sulfurized calcium phenate composition was an overbased sulfurized calcium phenate composition having a TPP content of about 8.0 wt. %.

TABLE 1

| Ex./Comp. Ex. | Molar Eq. Amine | Amine | Molar Eq. Aldehyde | Solvent, wt. % | Temp., °C. | Time, hrs | Final TPP, wt. % | % TPP Reduced |
|---|---|---|---|---|---|---|---|---|
| 2 | 10 | diethylamine | 10 | 50% toluene | 80 | 4 | 0.16 | 98.0 |
| 3 | 5 | diethylamine | 5 | 15% toluene | 80 | 4 | 0.18 | 97.8 |
| 4 | 10 | diethylamine | 10 | 40% 100N | 80 | 4 | 0.00 | 100.0 |
| 5 | 6 | diethylamine | 5 | 50% 100N | 80 | 4 | 0.10 | 98.8 |
| 6 | 5 | diethylamine | 5 | 50% 100N | 80 | 0.5 | 1.79 | 77.7 |
| 7 | 5 | diethylamine | 5 | 50% 100N | 80 | 5 | 0.17 | 97.9 |
| 8 | 5 | diethylamine | 5 | 50% 100N | 100 | 4 | 0.20 | 97.6 |
| 9 | 5 | diethylamine | 5 | 50% 100N | 180 | 4 | 1.64 | 79.6 |
| 10 | 5 | diethylamine | 5 | 50% 2-ethylhexanol | 80 | 4 | 0.24 | 97.0 |
| 11 | 5 | diethylamine | 5 | 50% decylalcohol | 80 | 4 | 0.14 | 98.3 |
| 12 | 5 | didodecylamine | 5 | 50% 100N | 80 | 4 | 0.08 | 99.1 |
| 13 | 5 | bis(2-ethylhexyl)amine | 5 | 50% 100N | 80 | 0.5 | 1.79 | 77.7 |
| 14 | 5 | bis(2-ethylhexyl)amine | 5 | 50% 100N | 80 | 5 | 1.17 | 85.4 |
| A | 2 | diethylamine | 2 | 50% 100N | 100 | 4 | 3.48 | 56.5 |
| B | 2 | diethylamine | 2 | 50% 100N | 120 | 4 | 4.89 | 38.9 |

EXAMPLES 15 TO 25 AND COMPARATIVE EXAMPLES C-E

The following examples were repeated in substantially the same manner as Example 1 using the reactants and reaction conditions as set forth below in Table 2. For the Following examples the source of formaldehyde was either paraformaldehyde (PF) or formalin (F) and the starting sulfurized calcium phenate composition was an overbased sulfurized calcium phenate composition having a TPP content of about 5.5 wt %.

TABLE 2

| Ex./Comp. Ex. | Molar Eq. Amine | Amine | Molar Eq. Aldehyde | Solvent, wt. % | Temp., °C. | Time, hrs | Final TPP, wt. % | % TPP Reduced |
|---|---|---|---|---|---|---|---|---|
| 15 | 5 | diethylamine | 5F | 50% 100N | 80 | 4 | 0.69 | 87.5 |
| 16 | 5 | diethylamine | 5PF | 50% 100N | 80 | 4 | 0.45 | 91.8 |
| 17 | 10 | diethylamine | 10F | 50% 100N | 80 | 4 | 0.08 | 98.6 |
| 18 | 10 | diethylamine | 10PF | 50% 100N | 100 | 4 | 0.05 | 99.2 |
| 19 | 2 | dimethylamine | 2F | 50% 100N | 80 | 4 | 0.95 | 82.8 |
| 20 | 5 | dimethylamine | 5F | 50% 100N | 80 | 4 | 0.11 | 98.1 |
| 21 | 10 | dimethylamine | 10F | 50% 100N | 80 | 4 | 0.00 | 100.0 |
| 22 | 2 | mono-methyl amine | 4.5PF | 15% toluene | 80 | 4 | 1.10 | 80.0 |
| 23 | 5 | didecylamine | 5PF | 80% toluene | 80 | 4 | 0.85 | 84.6 |
| 24 | 3 | diethylamine | 3PF | 15% toluene | 80 | 4 | 0.7 | 87.3 |
| 25 | 4 | diethylamine | 4PF | 15% toluene | 80 | 4 | 0.36 | 93.5 |
| C | 2 | diethylamine | 2F | 50% 100N | 80 | 4 | 2.48 | 55.0 |
| D | 2 | diethylamine | 2F | 15% 2ethylhexanol | 80 | 4 | 1.95 | 64.6 |
| E | 2 | diethyltriamine | 4.5PF | 15% toluene | 80 | 4 | 1.31 | 76.2 |

EXAMPLES 26 TO 29

The following examples were repeated in substantially the same manner as Example 1 using the reactants and reaction conditions as set forth below in Table 3. For each example, the source of formaldehyde was paraformaldehyde and the starting sulfurized calcium phenate composition was not overbased and had a TPP content of about 2.8 wt. %.

TABLE 3

| Ex./ Comp. Ex. | Molar Eq. Amine | Amine | Molar Eq. Aldehyde | Solvent, wt. % | Temp., °C. | Time, hrs | Final TPP, wt. % | % TPP Reduced |
|---|---|---|---|---|---|---|---|---|
| 26 | 1 | diethylamine | 1 | 100% benzene | 80 | 4 | 0.14 | 95.0 |
| 27 | 5 | diethylamine | 5 | 50% 100N | 80 | 0.5 | 0.00 | 100.0 |
| 28 | 5 | diethylamine | 5 | 50% 100N | 80 | 4 | 0.00 | 100.0 |
| 29 | 5 | diethylamine | 5 | 15% toluene | 80 | 4 | 0.14 | 95.0 |

EXAMPLE 30

Preparation of Mannich Post-Treated Tetrapropenyl Alkylphenol

To 150 g of tetrapropenylphenol (TPP) in a 1 liter three neck round bottom flask fitted with, a magnetic stirrer, condenser and nitrogen inlet was added 500 ml of anhydrous benzene. The solution was stirred vigorously under a nitrogen atmosphere at ambient temperature, and paraformaldehyde (19.55 g, 1.2 eq) was added, followed by addition of diethyl amine (67.9 ml, 1.2 eq) over a 5 minute period. The reaction mixture was heated to 80° C. for 4 hours, then cooled to ambient temperature. Ethyl acetate was then added (500 ml) and the reaction mixture was washed with 3×200 ml of 1N HCl dried over $MgSO_4$ and the solvent removed under reduced pressure.

The crude product was purified using flash column chromatography: $^1H$ NMR δ 0.2-1.9 (m, 31.9H, CH3, CH2), δ 2.51 (t, 4.0H, CH2), δ 3.7 (s, 2.0H, CH2-N), δ 6.5-7.3 (m, 3.0H, aromatic CH).

Testing

The objective of the study was to evaluate the ability of the mannich post-treated tetrapropenyl alkylphenol of Example 30, to demonstrate or mimic biological activities consistent with agonism of natural estrogens.

Procedure

In accordance with OECD Guideline No. 440, the OECD principles of GLP, and U.S. EPA GLP Standards (40 CFR, Parts 160 and 792), the mannich post-treated tetrapropenyl alkylphenol of Example 30 was administered orally by gavage to test groups of 6 ovariectomized female Crl:CD(SD) rats once daily for 3 consecutive days at 75, 250, 500, and 1000 mg/kg/day. A positive control group (17α-ethynylestradiol at 0.2 mg/kg/day) and a vehicle control group (corn oil) were also tested. Animals were euthanized by carbon dioxide inhalation approximately 24 hours following administration of the last dose, and a gross examination of the uterus was conducted; and uterine weights (wet and blotted) were recorded.

Results:

Body Weights

Significant ($p<0.05$ or $p<0.1$) mean body weight losses were noted in the animals (250, 500, and 1000 mg/kg/day treatment groups) treated with mannich post-treated tetrapropenyl alkylphenol of Example 30 and the positive control animals (0.2 mg/kg/day estradiol) compared to the mean body weight gains in the vehicle control animals over the treatment period, Uterine Weights As shown in FIG. 1, there was no significant difference in mean blotted or wet uterine weights at airy of the four treatment groups (75, 250, 500, and 1000 mg/kg/day) compared to the vehicle control group. Both mean blotted and wet uterine weights in the positive control group were significantly increased ($p<0.01$) compared to the vehicle control group, it is believed that TPP typically causes dose-dependent increase in uterine weights (1, 2, 3 and 7 fold at 75, 125, 250, and 500 mg/kg/day, respectively).

Conclusion

OECD Guideline No. 440 (Uterotropic Assay) indicates that a test should be considered positive if there is a statistical increase in uterine weight ($p<0.05$) when compared to vehicle control. Based on this guidance, the data suggests that the mannich post-treated tetrapropenyl alkylphenol of Example 30 does not appear to demonstrate or mimic the biological activity consistent with agonists of natural estrogen in the Uterotropic assay.

EXAMPLE 31

Preparation of Mannich Post Treated Sulfurized Calcium Phenate Composition

A reactor containing 418.6 grams of overbased sulfurized calcium phenate composition (commercially available from Chevron Oronite Company LLC) having a total TPP content of 5.5 wt. % was heated to a reaction temperature of 100° C. and 12.6 grams of solid para-formaldehyde was added. This mixture was stirred 5 minutes and then 30.5 grams of diethylamine was added over 3 minutes. The reaction mixture was held at 100° C. for 5 hours. The reaction was stripped by placed under vacuum (250 mm Hg) and heated to 130° C. and held there for 30 minutes. The vacuum was broken with nitrogen, the reaction allowed to cool to approximately 100° C. and the reactor contents isolated to afford 431.6 grams of crude product. A portion (214.9 grams) of the crude product was filtered with the aid of filter aid (Celite) to afford 187.7 grams of final product with, the following properties: TBN=260; wt. % Total. TPP=0.3; wt. %, % Ca=9.2, wt. % Sulfur=3.2, wt. % CO2=4.78, Volume % Sediment=0.01, wt % Nitrogen=0.35, Viscosity=504 cSt (100° C.) as determined by ASTM D445-88.

Repeating the above reaction while varying the reaction, temperature between 80° C. and 130° C.; the hold time between 3.5 hrs and 6 hrs; the stripping temperature between 110° C. and 130° C. and stripping vacuum between 250 mm Hg and 350 Hg; afforded filtered final, products with viscosities ranging from 389 cSt (110° C.) to 538 cSt (100° C.).

It will, be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A post-treated salt of a sulfurized alkyl-substituted hydroxyaromatic composition which is a reaction product of (a) a salt of a sulfurized alkyl-substituted hydroxyaromatic composition, wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof, (b) a source of an aldehyde and (c) a primary and/or secondary monoamine compound having at least one active hydrogen.

2. The post-treated salt of a sulfurized alkylhydroxyaromatic composition of claim 1, wherein the salt of a sulfurized alkyl-substituted hydroxyaromatic composition is produced by (i) alkylating a hydroxyaromatic compound with one or more olefins comprising $C_9$ to $C_{18}$ oligomers of monomers selected from propylene, butylene or mixtures thereof; and (ii) sulfurizing and neutralizing the alkyl-substituted hydroxyaromatic compound in any order.

3. The post-treated salt of a sulfurized alkylhydroxyaromatic composition of claim 1, wherein the salt of a sulfurized alkyl-substituted hydroxyaromatic composition is an overbased salt of a sulfurized alkyl-substituted hydroxyaromatic composition.

4. The post-treated salt of a sulfurized alkylhydroxyaromatic composition of claim 1, wherein the aldehyde is selected from the group consisting of formaldehyde, paraformaldehyde, formal in and mixtures thereof.

5. The post-treated salt of a sulfurized alkylhydroxyaromatic composition of claim 1, wherein the primary and/or secondary monoamine compound is a primary monoamine compound selected from the group consisting of methylamine, ethylamine, n-propylamine, isopropylamine, n-butylamine, isobutylamine, sec-butylamine, tert-butylamine, pentylamine, hexylamine, heptylamine, octylamine, nonylamine, decylamine, undecylamine, dodecylamine, tetradecylamine, hexadodecylamine, stearylamine, octadecylamine, eicosylamine, cyclopentylamine, cyclohexylamine, aniline, benzylamine, 2-aminotoluene, 3-aminotoluene, 4-aminotoluene, methanolamine, ethanolamine, 2,4-dimethylaniline, 2,3-dimethylaniline, 2,5-dimethylaniline, 2,6-dimethylaniline, 3,4-dimethylaniline, 3,5-dimethylaniline, 2,4,5-trimethylaniline, 2,4,6-trimethylaniline, 3,4,5,6-tetramethylaniline, 2,4,5,6-tetramethylaniline, 2,3,5,6-tetramethylaniline, 2-ethyl-3-hexylaniline, 2-ethyl-4-hexylaniline, 2-ethyl-S-hexylaniline, 2-ethyl-6-hexylaniline, 3-ethyl-4-hexylaniline, 3-ethyl-5-hexylaniline, 3-ethyl-2-hexylaniline, 4-ethyl-2-hexylaniline, 5-ethyl-2-hexylaniline, 6-ethyl-2-hexylaniline, 4-ethyl-3-hexylaniline, 5-ethyl-3-hexylaniline, 3,4,6-triethyltoluene, 2-methoxyaniline, 3-methoxyaniline, 4-methoxyaniline, 2-methoxy-3-methylaniline, 2-methoxy-4-methylaniline, 2-methoxy-5-methylaniline, 2-methoxy-6-methylaniline, 3-methoxy-2-methylaniline, 3-methoxy-4-methylaniline, 3-methoxy-5-methylaniline, 3-methoxy-6-methylaniline, 4-methoxy-2-methylaniline, 4-methoxy-3-methylaniline, 2-ethoxyaniline, 3-ethoxyaniline, 4-ethoxyaniline, 4-methoxy-5-methylaniline, 4-methoxy-6-methylaniline, 2-methoxy-3-ethylaniline, 2-methoxy-4-ethylaniline, 2-methoxy-5-ethylaniline, 2-methoxy-6-ethylaniline, 3-methoxy-2-ethylaniline, 3-methoxy-4-ethylaniline, 3-methoxy-5-ethylaniline, 3-methoxy-6-ethylaniline, 4-methoxy-2-ethylaniline, 4-methoxy-3-ethylaniline, 2-methoxy-2,3,4-trimethylaniline, 3-methoxy-2,4,5-trimethylaniline, 4-methoxy-2,3,5-trimethylaniline, and mixtures thereof.

6. The post-treated salt of a sulfurized alkylhydroxyaromatic composition of claim 1, wherein the primary and/or secondary monoamine compound is a secondary monoamine compound selected from the group consisting of dimethylamine, diethylamine, dipropylamine, dibutylamine, dipentylamine, dihexylamine, diheptylamine, dioctylamine, dinonylamine, didecylamine, diundecylamine, didodecylamine, ditetradecylamine, dihexadecylamine, dimethanolamine, diethanolamine, diphenylamine, dicyclohexylamine and mixtures thereof.

7. The post-treated salt of a sulfurized alkylhydroxyaromatic composition of claim 1, which is prepared by a process comprising:
(a) providing a salt of a sulfurized alkyl-substituted hydroxyaromatic composition containing an unsulfurized alkyl-substituted bydroxyaromatic compound and its unsulfurized metal salt; wherein the alkyl-substituted hydroxyaromatic compound is derived from alkylation of a hydroxyaromatic compound with one or more olefins comprising $C_9$ to $C_{18}$ oligomers of monomers selected from propylene, butylene or mixtures thereof, and
(b) reacting the salt of a sulfurized alkyl-substituted hydroxyaromatic composition with an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

8. The post-treated salt of a sulfurized alkylhydroxyaromatic compound of claim 7, having at least about 80% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

9. The post-treated salt of a sulfurized alkylhydroxyaromatic compound of claim 7, having at least about 90% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

10. A process for preparing a post-treated salt of a sulfurized alkyl-substituted hydroxyaromatic composition having a reduced content of unsulfurized alkyl-substituted hydroxyaromatic compound and its unsulfurized metal salt, the process comprising the steps of:
(a) providing a salt of a sulfurized alkyl-substituted hydroxyaromatic composition containing an unsulfurized alkyl-substituted hydroxyaromatic compound and its unsulfurized metal salt; wherein the alkyl-substituted hydroxyaromatic compound is derived from alkylation of a hydroxyaromatic compound with one or more olefins comprising C$_9$ to C$_{18}$ oligomers of monomers selected from propylene, butylene or mixtures thereof; and (b) reacting the salt of a sulfurized alkyl-substituted hydroxyaromatic composition with an effective amount of an aldehyde and a primary and/or secondary monoamine compound having at least one active hydrogen and under reaction conditions sufficient to provide a post-treated salt of the sulfurized alkyl-substituted hydroxyaromatic composition having at least about 70% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

11. The process of claim 10, wherein the salt of a sulfurized alkyl-substituted hydroxyaromatic composition provided in step (a) is an overbased salt of a sulfurized alkyl-substituted hydroxyaromatic composition.

12. The process of claim 10, wherein the aldehyde is selected from the group consisting of formaldehyde, paraformaldehyde, formalin and mixtures thereof and the primary and/or secondary monoamine compound is a primary monoamine compound selected from the group consisting of methylamine, ethylamine, n-propylamine, isopropylamine, n-butylamine, isobutylamine, sec-butylamine, tert-butylamine, pentylamine, hexylamine, heptylamine, octylamine, nonylamine, decylamine, undecylamine, dodecylamine, tetradecylamine, hexadodecylamine, stearylamine, octadecylamine, eicosylamine, cyclopentylamine, cyclohexylamine, aniline, benzylamine, 2-aminotoluene, 3-aminotoluene, 4-aminotoluene, methanolamine, ethanolamine, 2,4-dimethylaniline, 2,3-dimethylaniline, 2,5-dimethylaniline, 2,6-dimethylaniline, 3,4-dimethylaniline, 3,5-dimethylaniline, 2,4,5-trimethylaniline, 2,4,6-trimethylaniline, 3,4,5,6-tetramethylaniline, 2,4,5,6-tetramethylaniline, 2,3,5,6-tetramethylaniline, 2-ethyl-3-hexylaniline, 2-ethyl-4-hexylaniline, 2-ethyl-5-hexylaniline, 2-ethyl-6-hexylaniline, 3-ethyl-4-hexylaniline, 3-ethyl-5-hexylaniline, 3-ethyl-2-hexylaniline, 4-ethyl-2-hexylaniline, 5-ethyl-2-hexylaniline, 6-ethyl-2-hexylaniline, 4-ethyl-3-hexylaniline, 5-ethyl-3-hexylaniline, 3,4,6-triethyltoluene, 2-methoxyaniline, 3-methoxyaniline, 4-methoxyaniline, 2-methoxy-3-methylaniline, 2-methoxy-4-methylaniline, 2-methoxy-5-methylaniline, 2-methoxy-6-methylaniline, 3-methoxy-2-methylaniline, 3-methoxy-4-methylaniline, 3-methoxy-5-methylaniline, 3-methoxy-6-methylaniline, 4-methoxy-2-methylaniline, 4-methoxy-3-methylaniline, 2-ethoxyaniline, 3-ethoxyaniline, 4-ethoxyaniline, 4-methoxy-5-methylaniline, 4-methoxy-6-methylaniline, 2-methoxy-3-ethylaniline, 2-methoxy-4-ethylaniline, 2-methoxy-5-ethylaniline, 2-methoxy-6-ethylaniline, 3-methoxy-2-ethylaniline, 3-methoxy-4-ethylaniline, 3-methoxy-S-ethylaniline, 3-methoxy-6-ethylaniline, 4-methoxy-2-ethylaniline, 4-methoxy-3-ethylaniline, 2-methoxy-2,3,4-trimethylaniline, 3-methoxy-2,4,5-trimethylaniline, 4-methoxy-2,3,5-trimethylaniline, and mixtures thereof.

13. The process of claim 10, wherein the aldehyde is selected from the group consisting of formaldehyde, paraformaldehyde, formalin and mixtures thereof and the primary and/or secondary monoamine compound is a secondary monoamine compound selected from the group consisting of dimethylamine, diethylamine, dipropylamine, dibutylamine, dipentylamine, dihexylamine, diheptylamine, dioctylamine, dinonylamine, didecylamine, diundecylamine, didodecylamine, ditetradecylamine, dihexadecylamine, dimethanolamine, diethanolamine, diphenylamine, dicyclohexylamine and mixtures thereof.

14. The process of claim 10, wherein the effective amount of the aldehyde is from about 1 molar equivalent to about 10 molar equivalent per equivalent of the unsulfurized alkyl-substituted hydroxyaromatic compound and its unsulfurized metal salt present in the salt of a sulfurized alkyl-substituted hydroxyaromatic composition provided in step (a), and the effective amount of the monoamine compound is from about 1 molar equivalent to about 10 molar equivalent per equivalent of the unsulfurized alkyl-substituted hydroxyaromatic compound and its unsulfurized metal salt present in the salt of a sulfurized alkyl-substituted hydroxyaromatic composition provided in step (a).

15. The process of claim 10, wherein the reaction conditions include a temperature ranging from about 70° C. to about 180° C. and a time period ranging from about 30 minutes to about 14 hours.

16. The process of claim 10, wherein the post-treated salt of the sulfurized alkyl-substituted hydroxyaromatic composition has at least about 80% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

17. The process of claim 10, wherein the post-treated salt of the sulfurized alkyl-substituted hydroxyaromatic composition has at least about 90% reduced content, by combined mass, of the unsulfurized alkyl-substituted hydroxyaromatic compound and its unsulfurized metal salt, compared to the content, by combined mass, of the unsulfurized alkyl-substituted hydroxyaromatic compound and its unsulfurized metal salt present in the non-post-treated salt of a sulfurized alkyl-substituted hydroxyaromatic composition.

18. A lubricating oil composition comprising (a) a major amount of an oil of lubricating viscosity and (b) at least one post-treated salt of a sulfurized alkylhydroxyaromatic compound of claim 1.

19. A lubricating oil composition comprising (a) a major amount of an oil of lubricating viscosity and (b) at least one post-treated salt of a sulfurized alkylhydroxyaromatic compound of claim 7.

20. A lubricating oil composition comprising (a) a major amount of an oil of lubricating viscosity and (b) at least one post-treated salt of a sulfurized alkylhydroxyaromatic compound of claim 8.

21. The lubricating oil composition of claim 18, wherein the at least one post-treated salt of a sulfurized alkylhydroxyaromatic compound is present in an amount of about 0.01 wt. % to about 10 wt. %, based on the total weight of the lubricating oil composition.

22. The lubricating oil composition of claim 18, further comprising at least one additive selected from the group consisting of an antioxidant, anti-wear agent, detergent, rust inhibitor, dehazing agent, demulsifying agent, metal deactivating agent, friction modifier, pour point depressant, antifoaming agent, co-solvent, package compatibiliser, corrosion-inhibitor, ashless dispersant, dye, extreme pressure agent and mixtures thereof.

23. A method for lubricating an engine comprising operating the engine with the lubricating oil composition of claim 18.

24. A method for reducing the endocrine disrupting properties of a lubricating oil composition on exposure to mammals, the method comprising adding at least one post-treated salt of a sulfurized alkyl-substituted hydroxyaromatic composition of claim 1, to a lubricating oil composition comprising a major amount of an oil of lubricating viscosity.

25. A method for reducing the endocrine disrupting properties of a lubricating oil composition on exposure to mammals, the method comprising adding at least one post-treated salt of a sulfurized alkyl-substituted hydroxyaromatic composition of claim 7, to a lubricating oil composition comprising a major amount of an oil of lubricating viscosity.

* * * * *